United States Patent [19]
Scrantz

[11] Patent Number: 5,619,423
[45] Date of Patent: Apr. 8, 1997

[54] SYSTEM, METHOD AND APPARATUS FOR THE ULTRASONIC INSPECTION OF LIQUID FILLED TUBULARS AND VESSELS

[76] Inventor: Leonard Scrantz, P.O. Box 1145, Breaux Bridge, La. 70517

[21] Appl. No.: 183,747

[22] Filed: Jan. 21, 1994

[51] Int. Cl.[6] .................................................. G01B 7/06
[52] U.S. Cl. ........................ 364/507; 73/622; 73/638; 324/220; 324/229; 324/240; 364/506; 364/563
[58] Field of Search .................................... 73/622, 638, 643, 73/865.8; 324/220, 229, 240, 242; 364/506, 507, 563

[56] References Cited

U.S. PATENT DOCUMENTS

| | | | |
|---|---|---|---|
| H879 | 1/1991 | Vernon et al. | 324/240 |
| 4,092,868 | 6/1978 | Thompson et al. | 73/638 |
| 4,307,615 | 12/1981 | Robinson | 73/643 |
| 4,314,479 | 2/1982 | Spijkerman | 73/643 |
| 4,353,257 | 10/1982 | Vrba et al. | 73/623 |
| 4,691,572 | 9/1987 | Van den Berg et al. | 73/638 |
| 4,793,185 | 12/1988 | Boettger et al. | 73/643 |
| 4,855,676 | 8/1989 | Cecco et al. | 324/240 |
| 4,872,130 | 10/1989 | Pagano | 364/507 |
| 4,964,054 | 10/1990 | Sugaya et al. | 364/507 |
| 5,117,182 | 5/1992 | Cecco et al. | 324/240 |
| 5,161,413 | 11/1992 | Junker et al. | 73/634 |
| 5,429,009 | 7/1995 | Wolfe et al. | 73/865.8 |
| 5,439,157 | 8/1995 | Geier et al. | 73/643 X |
| 5,473,953 | 12/1995 | Appel | 73/635 X |
| 5,503,020 | 4/1996 | Mandracchia | 73/643 |
| 5,535,628 | 7/1996 | Rutherford | 73/622 |

*Primary Examiner*—Edward R. Cosimano
*Attorney, Agent, or Firm*—Robert Montgomery

[57] ABSTRACT

The invention relates to an improved system, method and apparatus for the external ultrasonic inspection of fluidized tubulars and tanks. The apparatus utilizes couplantless, contactless, computer controlled, Electromagnetic Acoustic Transducer (EMAT) probes for the external, longitudinal, scanning process. Thereby, detecting thin spots and other flaws along the circumferential belts of a pipe or tank without the need to encircle the pipe or tank with an array of transducers. The invention discloses a method of operation whereby the probe detects flaws in welds and the pipe walls by launching and receiving simultaneous ultrasonic signals, circumferentially around a pipe, from the same transducer.

39 Claims, 14 Drawing Sheets

SYSTEM, METHOD AND APPARATUS FOR THE ULTRASONIC INSPECTION OF LIQUID FILLED TUBULARS AND VESSELS

BACKGROUND OF THE INVENTION

1. FIELD OF THE INVENTION

The instant invention relates to an improved method and apparatus for the ultrasonic inspection of pipe and tanks. More particular, the invention relates to a couplantless apparatus used for the external, longitudinal detection of defects such as cracks and thin spots in the circumferential belts of pipe or tank walls without the need to encircle the pipe or tank with an array of transducers. The instant invention further relates to a method of operation whereby a computer Controlled Electromagnetic Acoustic Transducer (EMAT) system is utilized for transmitting and receiving ultrasonic beams induced through a tank wall or circumferentially around a pipe wall while traveling longitudinally along the length of the pipe or tank to detect thin spots without the use of a liquid couplant.

2. GENERAL BACKGROUND

One of the most widely used techniques for non-destructive evaluation of tubular members, such as steel pipe, involves the use of sonic beams of ultrasonic frequencies. Typically, the apparatus employed in such techniques includes a piezoelectric crystal which produces ultrasonic vibrations in response to the application of a regulated voltage. When inspecting a tubular member or pipe for flaws or wall thinning, such techniques routinely rely on a method whereby such an apparatus, called a transducer, is maintained in a position relative to the pipe surface and produces ultrasonic waves for coupling through a flowing column of liquid to the pipe. In order to overcome the limitations of a large fixed array of transducers, surrounding the pipe with a couplant or, the inability in certain field situations, to maneuver the pipe into such an array, it was theorized in the prior art that better results could be obtained through the use of an electromagnetic acoustic transducer (EMAT) which would eliminate the use of a liquid couplant, and the need of the apparatus to encircle the pipe. Thus, EMATS have been found effective in launching and detecting ultrasonic waves across a small air gap by the electromagnetic induction process and can operate on rough and unprepared surfaces.

Various means have been employed utilizing EMAT'S for inducing detectable waves into metal for pipe inspection purposes. U.S. Pat. No. 4,092,868 discloses a means for inducing Lamb Waves electromagnetically into a metal object to be inspected. Such waves fill the entire cross section of the material rather than a narrow beam of ultrasonic energy. However, the device as disclosed is incapable of focusing such ultrasonic energy in the object under inspection. Although Thompson in U.S. Pat. No. 4,092,868 teaches a method of internal pipe inspection utilizing ultrasonic transducers in cooperation with Lamb Waves to detect defects in a pipe line, it still relies on two separate receiver coils located within north-south magnets, located at a predetermined circumferential distance apart. Therefore, defects can only be detected between the two magnets and their receivers.

U.S. Pat. No. 4,691,572 issued to van den Berg et al. discloses the use of ultrasonic electromagnetic transducers for the internal inspection of pipelines which requires no acoustic compliant between the transducer and the tube wall. Van den Berg et al. further teaches the applicability of ultrasonic, electromagnetic transducers in an apparatus used for internal pipe inspection which is not restricted to the use of Lamb Waves but is also effective when elastic shear waves are generated in the tubular walls. It is here that the similarity between the present invention and that of van den Berg et al. ends. Van den Berg teaches away from the present invention by advocating the detection of the ultrasonic waves, by a receiver coil located around the south pole of the permanent magnet, after being reflected against the exterior surface of the pipe wall. He also indicates that the south pole should be in near proximity to the pipe surface. These and other distinctions will become more apparent in the following disclosure. The related prior art does not suggest any means of electrically driving or controlling the scanner along the pipe being inspected. Nor does the prior art disclose an external method of inspecting a pipe line for defects when the pipe is charged.

The design of electromagnetic acoustic transducers and their application in pipeline inspection remains a somewhat empirical art, and a great many promising constructions have been proposed, tried and abandoned. As a consequence of the above noted development of the art, the requirements for a low cost, low noise, mechanically simple, and inexpensive apparatus and procedure is apparent. It is to this apparent need that the present invention addresses itself.

SUMMARY OF THE PRESENT INVENTION

The present invention is intended for use as an EMAT flaw detection system for the full circumference inspection of in-service refinery piping and oil industry tubular goods. In the petrochemical industry, there are miles of pipe carrying various liquids that are subject to corrosion and fatigue damage at random locations. Often, these locations are found by judicious maintenance planning or luck, but more often they are discovered by the development of small leaks that appear during the normal operation of the plant. If the pipes could be inspected on a routine basis, the leaks could be prevented and repairs scheduled for convenient times. Unfortunately, such an inspection must be done quickly by a minimal crew; and the sensors must be able to operate in remote locations on pipes and, on occasion, at elevated temperatures and with a wide variety of surface conditions. In recent years, a new kind of ultrasonic, transducer technology has been developed which operates without a liquid couplant. Such transducers have been applied to inspecting buried gas pipelines, railroad tracks and the products of steel mills where speed of inspection and operation on rough, rusty surfaces are the norm. Thus, such technology seems to be well suited to the application of rapid inspection of long runs of tubular piping such as may be found in refineries. Such transducers called Electromagnetic Acoustic Transducers or EMATs operate by an electromagnetic induction process across a small air gap. EMATs usually consist of a magnet and a coil of wire held close to the surface of the part to be interrogated with ultrasonic waves. They can operate on any metal or ferromagnetic material, like steel, without careful alignment or a skilled operator. More important, they can be designed to excite and detect ultrasonic wave types that are optimal for the desired inspection process. It is this latter feature that makes them so useful for the piping inspection problem. Electromagnetic transducers derive their name from the fact that they can excite and detect ultrasonic vibrations in metals by an electromagnetic induction process across a small air gap. Thus, they operate as ultrasonic transducers without any water bath, squirter or grease couplants. This opens up a wide variety of applications that are not available to conventional, piezoelectric transducers techniques such as inspections at high speeds, elevated temperatures, or parts with complex geometries.

An EMAT in its most elementary form consists of a loop of wires held close to the surface of a metal part and a magnet that floods the area around the loop with a magnetic field. Their versatility for generating and detecting different kinds of ultrasonic waves comes from the many different shapes that the coil can take combined with the fact that the coil can be either parallel or perpendicular to the surface. An alternating current in the transmitter coil induces an alternating eddy current in the surface that finds itself flowing through a magnetic field. This combination of alternating eddy current and magnetic field exerts an alternating force on the surface that launches the ultrasonic wave. It will be a shear wave if the magnetic field is perpendicular to the surface and a longitudinal wave if the field is parallel to the surface. When acting as a receiver, the EMAT performs like an electrical generator because the ultrasonic waves cause the surface of the material to vibrate in the presence of the magnetic field and this motion generates an alternating current in the surface. By magnetic induction, the nearby coil senses this current and outputs a voltage which is proportional to the velocity at which the surface is moving.

The efficiency of EMATs is measured by the voltage output of a receiver coil reacting to sound waves from a transmitter coil through which a unit of current is flowing. For normal values of the parameters, the generation of a millivolt of output voltage demands the insertion of a few hundred amperes of transmitter current, hence, the need for special pulsar circuits to drive the EMAT coils in an electromagnetic transducer inspection system. It is, therefore, the improved design and further development of the EMAT Technology and its application to pipe inspection that the present invention addresses itself.

It is an object of the present invention to provide an improved electromagnetic acoustic transducer inspection system for the external inspection of pipe in general as well as linear welds in vessels.

It is a further object of the present invention to provide a method and apparatus for evaluating non-uniformities in metal utilizing a variety of ultrasonic waves as the application may demand.

It is still a further object of the present invention to provide an improved EMAT system which utilizes a computer to control, generate, calculate and assimilate data gained from multiple signal wave forms launched throughout the entire circumferential belting of a pipe.

It is another object of the present invention to provide a portable inspection method and apparatus for the rapid, external, tangential inspection of pipe by utilizing an electromagnetic acoustic transducer in conjunction with waves launched in both directions simultaneously around the circumference of a pipe to detect flaws which may be oriented in any direction.

These and other objects and the working features of the present invention will be apparent from the following detailed description, taken with reference to the accompanying drawings.

BRIEF DESCRIPTION OF THE DRAWINGS

FIG. 6b is a cross section view of the second embodiment of the transducer module shown in FIG. 6a;

DETAILED DESCRIPTION OF THE PREFERRED EMBODIMENT

Figure 1:
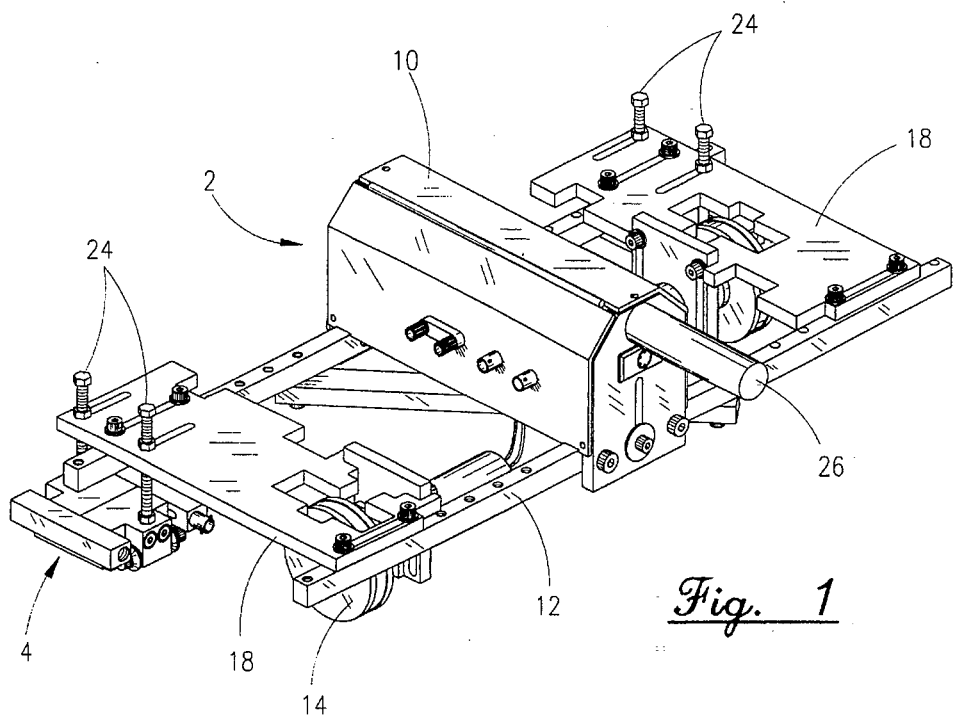
FIG. 1 is an isometric view of the preferred embodiment of a carriage probe having two transducers.
Figure 2:
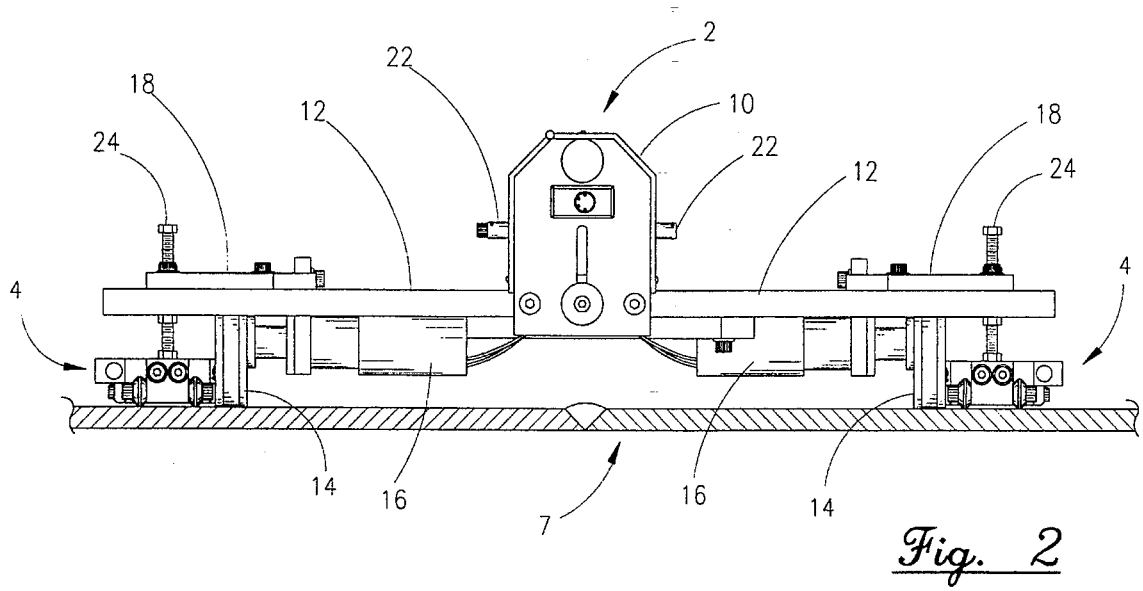
FIG. 2 is an end elevation view of the preferred embodiment wherein the articulated frame of the carriage is shown in a flat or horizontal plane as when inspecting a plate weld.
Figure 3:
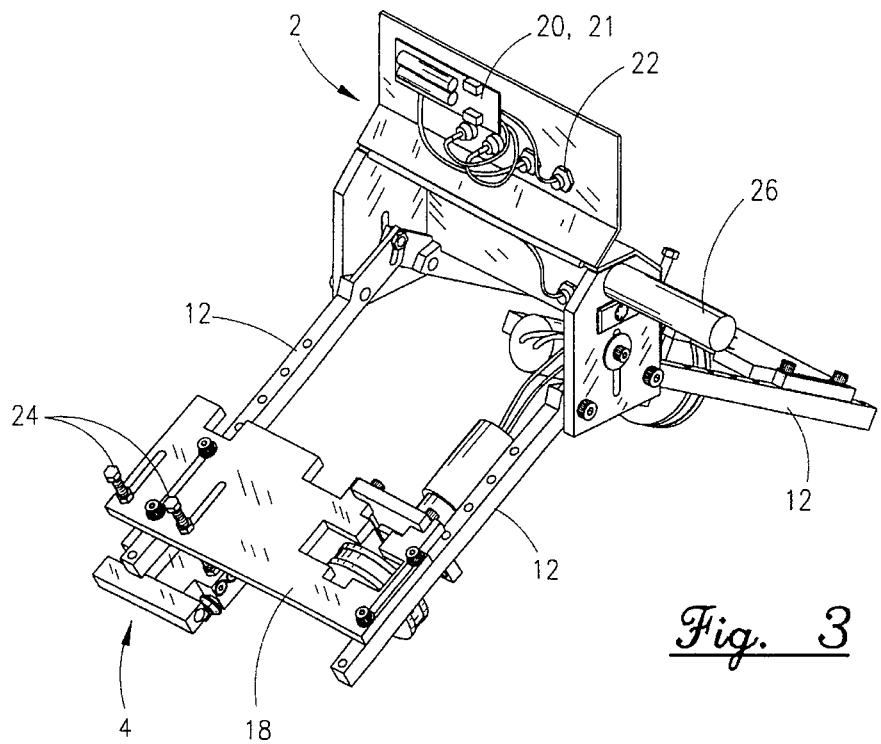
FIG. 3 is an isometric view of the preferred embodiment of the carriage probe shown with the articulated frame in the inverted, articulated position.
Figure 4:
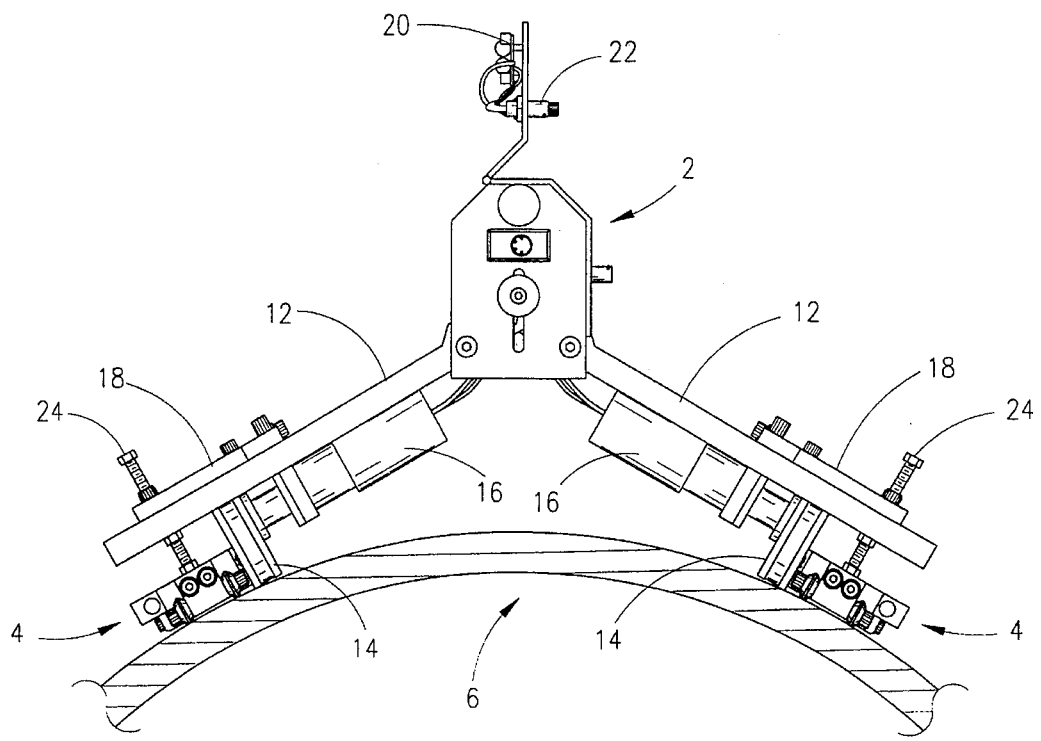
FIG. 4 is an end elevation view of the preferred embodiment of the carriage probe shown in the working position on a tubular member.
Figure 5:
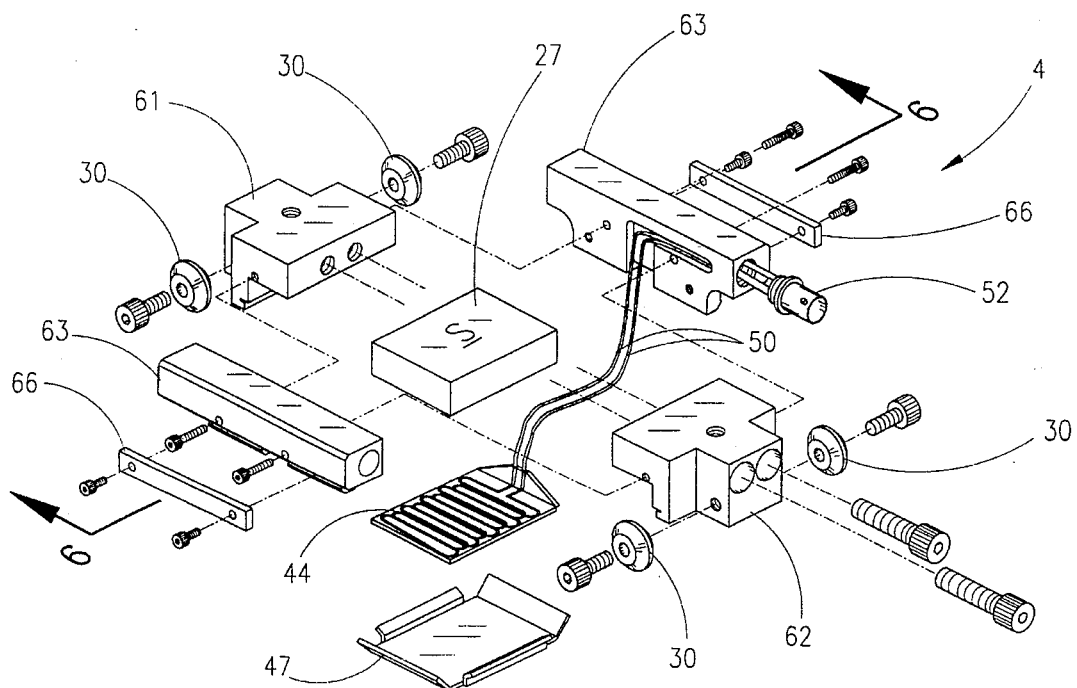
FIG. 5 is an exploded view of one embodiment of the transducer module.
Figure 6:
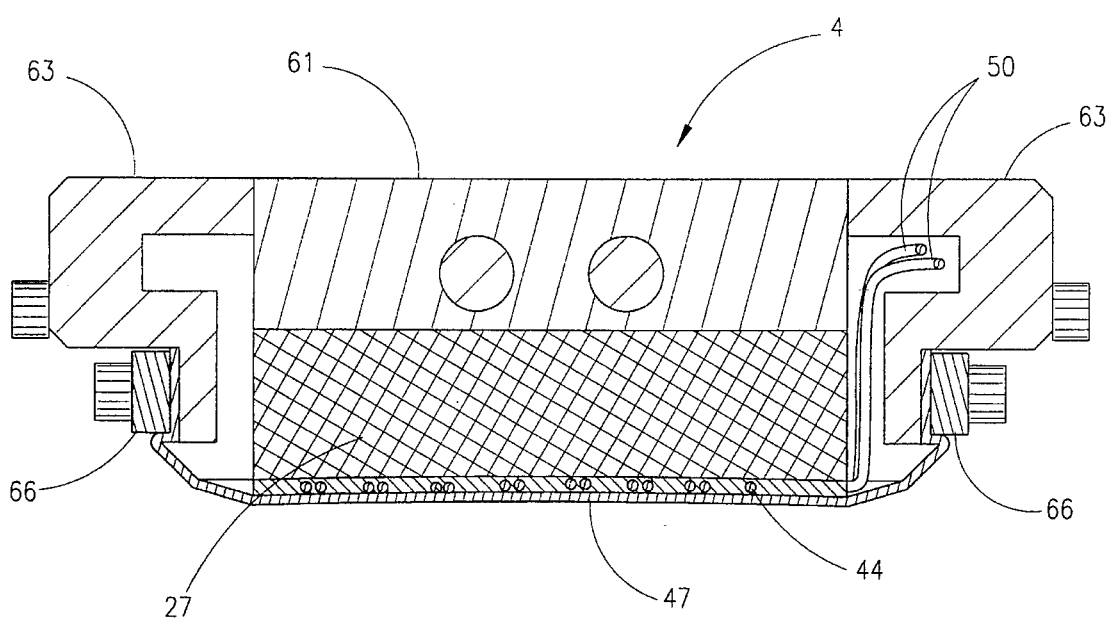
FIG. 6 is a cross section view of the transducer module depicted in FIG. 5.
Figure 6A:
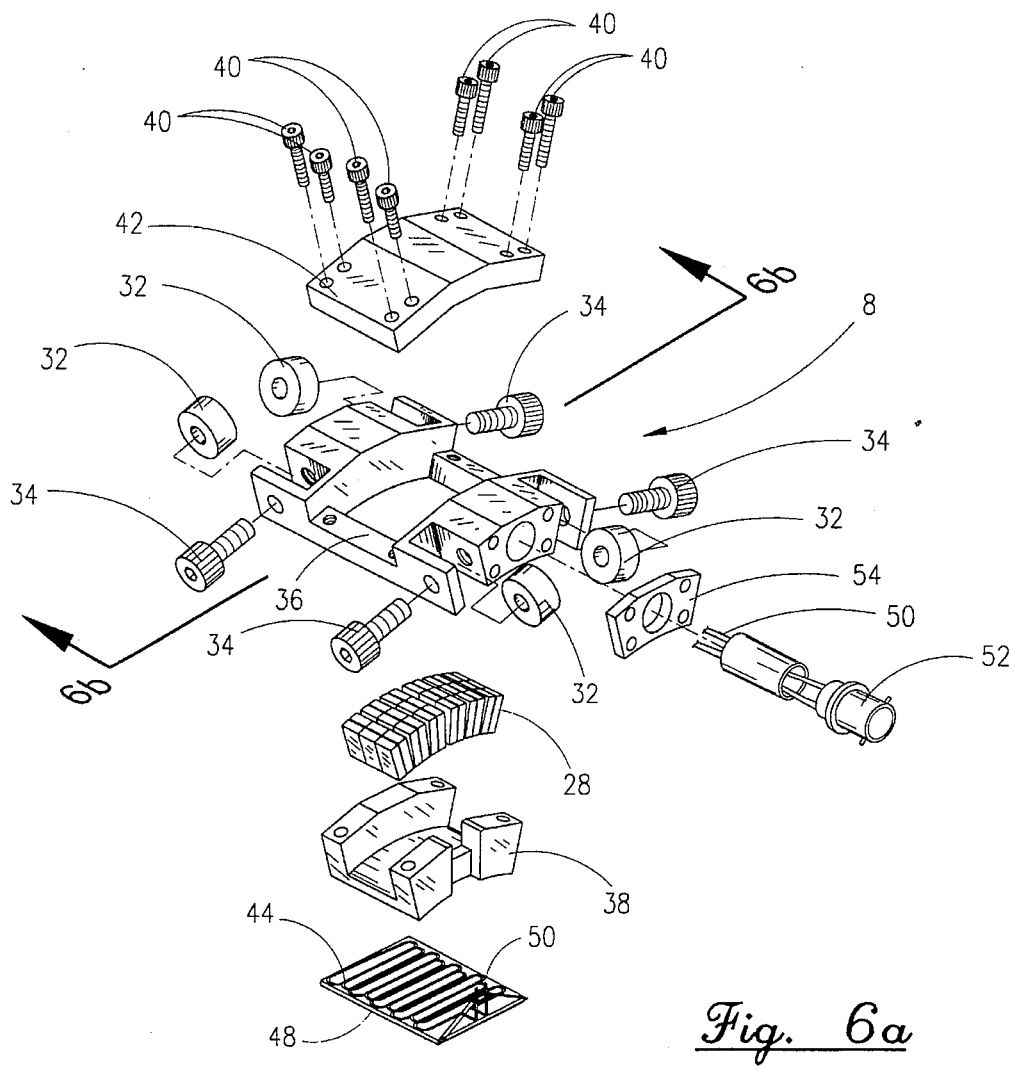
FIG. 6a is an exploded view of a second embodiment of the transducer module.

The Electromagnetic Acoustic Transducer (EMAT) 4 is a stand alone probe, or it can be carried onboard a carriage 2 which also includes a central body 10. The body 10 houses a portion of the electronic circuitry 20,21 and provides the electrical connection points 22 for one or more transducers 4. These connections 22 further provide connection points for connecting an umbilical cord 81 between the carriage 2 and the main control chassis 71. An adjustable, articulated frame 12 as shown in FIGS. 1–4, is centrally attached to the body housing 10, providing a mounting platform for the transducers 4. The articulated frame 12 allows the transducers 4 to be positioned in the flat plane, as seen in FIGS. 1 and 2, for inspecting large metal tank plates 7 and the like having only a slight curvature, or they may be adjusted for use on large diameter ferrous metal pipe 6 as seen in FIG. 4. This adjustment allows for up to 90 degrees orientation each of the transducers 4 on the pipe 6 if necessary. The carriage 2 may be propelled along the inspecting surface 6 or 7 by a set of magnetic wheels 14 driven by remotely controlled synchronous motors 16. The transducers 4 are mounted on plates 18 which are also incrementally adjustable along either side of the articulated frame 12 extending outwardly from the central body housing 10. The transducers 4 are secured to the mounting plates 18 and are adjustable laterally and vertically by a pair of jacking screws 24. A handle 26 is also provided for leverage in extracting the carriage 2 from the inspection surface 6 or 7 due to the strong magnetic attraction of the transducers 4 and the magnetic wheels 14. The Electromagnetic Acoustic Transducers (EMAT) 4 as seen in FIGS. 5 and 6a are equipped with permanent magnets 28 that supply the magnetic field for the EMAT transduction system. These magnets 28 are attracted to the pipe 6 with a very large force. Therefore, it is essential that the transducer probes 4 be mounted on wheels 30,32 as shown in FIGS. 5 and 6a, so they can be moved along the length of the pipe 6 during inspection as best seen in FIG. 4.

Figure 6B:
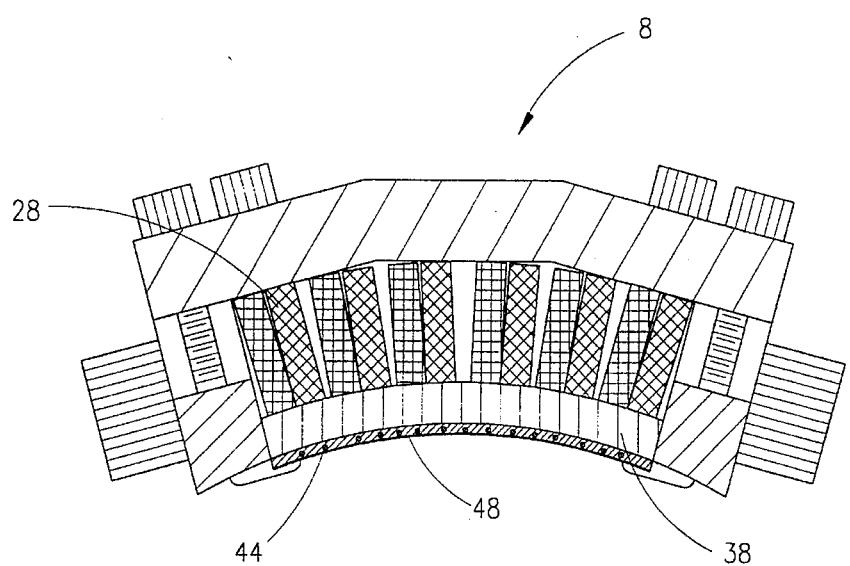
Figure 7:
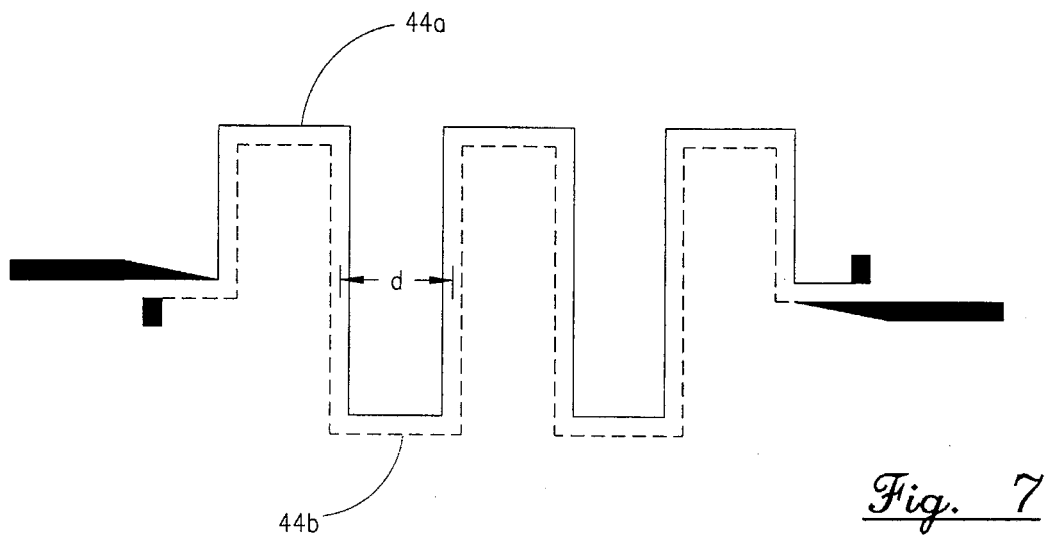
FIG. 7 is a top view of the transmitter and receiver coil arrangement on the upper side of the mylar separator sheet.
Figure 8:
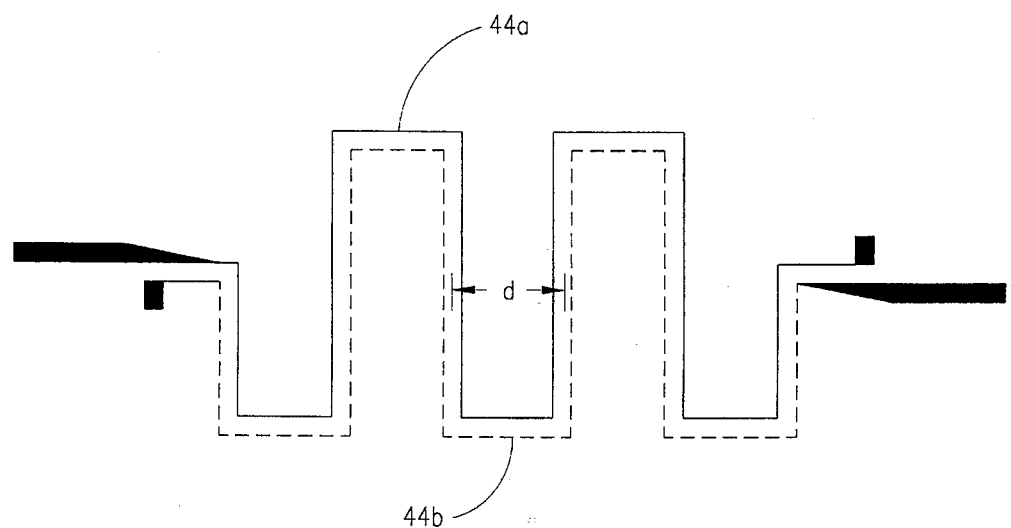
FIG. 8 is a top view of the transmitter and receiver coil arrangement on the lower side of the mylar separator sheet.

FIG. 6(b) shows the cross sectional end view of one embodiment 8 of the transducer whereby the lower surface of the magnet block 28 is curved in a manner to conform with the curvature of the pipe 6 under inspection. Thus, the wheels 32 are camable and adjusted to the pipe radius by allen head screws 34. This embodiment 8 has a main body portion 36 to which all components are attached. This embodiment utilizes a magnet module 38 for carrying a set of magnetic squares 28 arranged in pairs along three rows of twelve each, held in a semi-circular position by epoxy. The module 38 is secured to the main body 35 by screws 40 passing through the main body 36 cover plate 42. The transmitter and receiver (transceiver) coils 44(a)(b) arranged in an interrelated manner as shown in FIGS. 7 and 8 are secured to the inside of a titanium wear strip 48 which is attached to the under side of the magnet module 38. The coil wires 50 are passed through a cavity in the main body 36 to an electrical jack connector 52 which is secured to the main body 36 by a retainer plate 54.

The embodiment exemplified in FIG. 5 is comprised of head and tail blocks 61,62 bolted to each other, and a pair of side rails 63 having cavities therein bolted to both the head and tail blocks 61,62. A block magnet 27 is also disposed in a clamped relationship integrally within the confines of the head block 61, tail block 62 and side rails 63. The transmitter and receiver coils 44 are disposed along the exposed face of the block magnet 27, the ends of which extend into cavities provided along the inside of the side rails 63 culminating in electrical jack connections 52 recessed into the ends. A wear sheet 47 is also provided effectively covering the coils 44 and the block magnet 27. The wear sheet 47 is springably secured to each of the side rails by bar clamps and is maintained in sliding contact with the pipe or plate 6 or 7. This transducer embodiment 4 further utilizes a set of beveled vee wheels 30 attached to each end of the head and tail blocks 61,62. The block magnet 27 shown in FIG. 5 and 6 is a Neodymium-Iron Boron, with an energy product of at least 35 MGO and is sometimes machined with a slight curve on one face. When the titanium sheet 47,48 wears through, it and the coils 44 attached to it can be easily replaced by simply releasing the bar clamps 66 for transducer embodiment 4 shown in FIG. 5 or the cover screws 40 for transducer embodiment 8 shown in FIG. 6a.

A cross sectional view of the assembled interior of each of the transducer embodiments 4 or 8 shown in FIG. 6 and 6b. In FIG. 6b the section view exposes the permanent magnets 28 which are individual metal disk slabs approximately ⅛ inch thick by ½ inch tall by ½ inch deep. There are three rows of 12 slabs across the width to make a total of 36 individual magnets. Each is magnetized along the ½ inch dimension and in a manner so that all north poles face the pipe. The most suitable material for the magnets for this application has been found to be Neodymium-Iron-Boron with an energy product of 35 MGO.

An array of small magnets 28 glued together with epoxy was chosen to produce the significant curvature needed for smaller pipe, thereby avoiding the expense of a custom machined magnet for each pipe curvature. Wires leading from the interposed transmitter and receiver coils 44 connect the EMAT to the electronic connector 52 as seen in FIG. 5. The beveled or vee wheels 30 located at each end of the transducer, shown in FIG. 5, establish a clearance of about ¹⁄₁₆ inch between the titanium wear plate 48 and the pipe surface 6. This clearance allows the EMAT 4 and the springable titanium plate 47 to slide easily over any dirt, rust and burrs that may be on the pipe's 6 surface.

The internal construction of the EMAT's coils 44 is very important because it determines the frequency of operation and the sensitivity to thickness changes. Since the magnetic field is applied over a 1.5 inch square area, the outer dimensions of the coils 44 were chosen to match this area. Since the invention is capable of operation with only one EMAT, it is important to note that the transmitter coil and the receiver coil are interposed in close proximity, as shown in FIGS. 7,8, housed together in the same space. In particular, it is essential that the coil wires 44a, 44b must be coincident so the clockwise and counterclockwise signals, which are launched together by the transmitter coil, 44(a) will coincide exactly when they meet under the receiver coil 44(b) after each trip around the circumference. This has been accomplished by deploying the wires in the coils 44a, 44b on the top and bottom faces of an insulating Mylar sheet in the manner illustrated by FIGS. 7 and 8. FIG. 7 shows the top surface of the Mylar with the transmitter conductor 44a drawn as a solid line along a meandering line path from a large soldering pad on the left to a small pad on the right. The receiver coil 44b is shown as a dashed line that follows the same path but joins a large pad on the right to a small pad on the left. FIG. 8 shows the conductor path on the bottom surface as viewed from the top surface as if the Mylar were transparent. Here again the transmitter coil 44a is depicted by a solid line and the receiver coil wire 44b by a dashed line. By cutting the Mylar near the small pads and connecting the top and bottom pads together with a small wire, the top and bottom coils can be connected to make a continuous circuit of the solid (transmitter) and dashed (receiver) lines with the big pads which act as the connection points for wires that connect the coils to the transmitter and receiver connectors 52 located on opposite sides of the EMAT.

The most critical aspect of the EMAT coil arrangement is the dimensional spacing between the transmitter and receiver coils 44a, 44b arranged in a meandering shape. As seen in FIGS. 7 and 8 the dimension (d), sets the wave length of the Lamb wave that is launched or detected by the EMAT coil and determines the frequency of operation and the sensitivity to wall thickness changes in the inspection surface. Specifically, the wave length, "$\lambda$", is twice the coil wire spacing, "d". It is subsequently shown herein that the optimum ratio of pipe wall thickness to wire spacing for the Lamb wave inspection of tubulars is between 1.3 and 1.4. Thus, it would appear that a special EMAT coil is demanded for each wall thickness value. However, it has been found that one wire spacing can be used over a wide range of wall thicknesses just as one magnet curvature can operate over a range of pipe diameters. The table below indicates that probes with only two curvatures and EMAT coils with only three wire spacings need to be provided which will cover the total range of pipes usually encountered in the oil and chemical refinery industry.

TABLE I

Pipe dimensions expected to be encountered in refinery pipe inspections and the dimensions of probes and EMAT coils to be used on these pipes.

| SCHEDULE | O.D. inches | WALL THICK. inches | MAGNET. CURV. (Radius in.) | WIRE SPACE "d" (in) | T/d Ratio |
|---|---|---|---|---|---|
| 40 | 2.375 | 0.154 | 1.5 | 0.14 | 1.2 |
| 80 | " | 0.218 | " | " | 1.7 |
| 40 | 3.5 | 0.216 | " | " | 1.7 |
| 80 | " | 0.300 | " | 0.20 | 1.5 |
| 40 | 4.5 | 0.237 | 2.5 | " | 1.2 |
| 80 | " | 0.337 | " | " | 1.7 |
| 40 | 6.675 | 0.280 | " | " | 1.4 |
| 80 | " | 0.432 | " | 0.30 | 1.4 |
| 40 | 8.625 | 0.322 | " | 0.20 | 1.6 |
| 80 | " | 0.500 | " | 0.30 | 1.7 |
| 40 | 10.75 | 0.365 | " | " | 1.2 |
| 80 | " | 0.500 | " | " | 1.7 |

Figure 9:
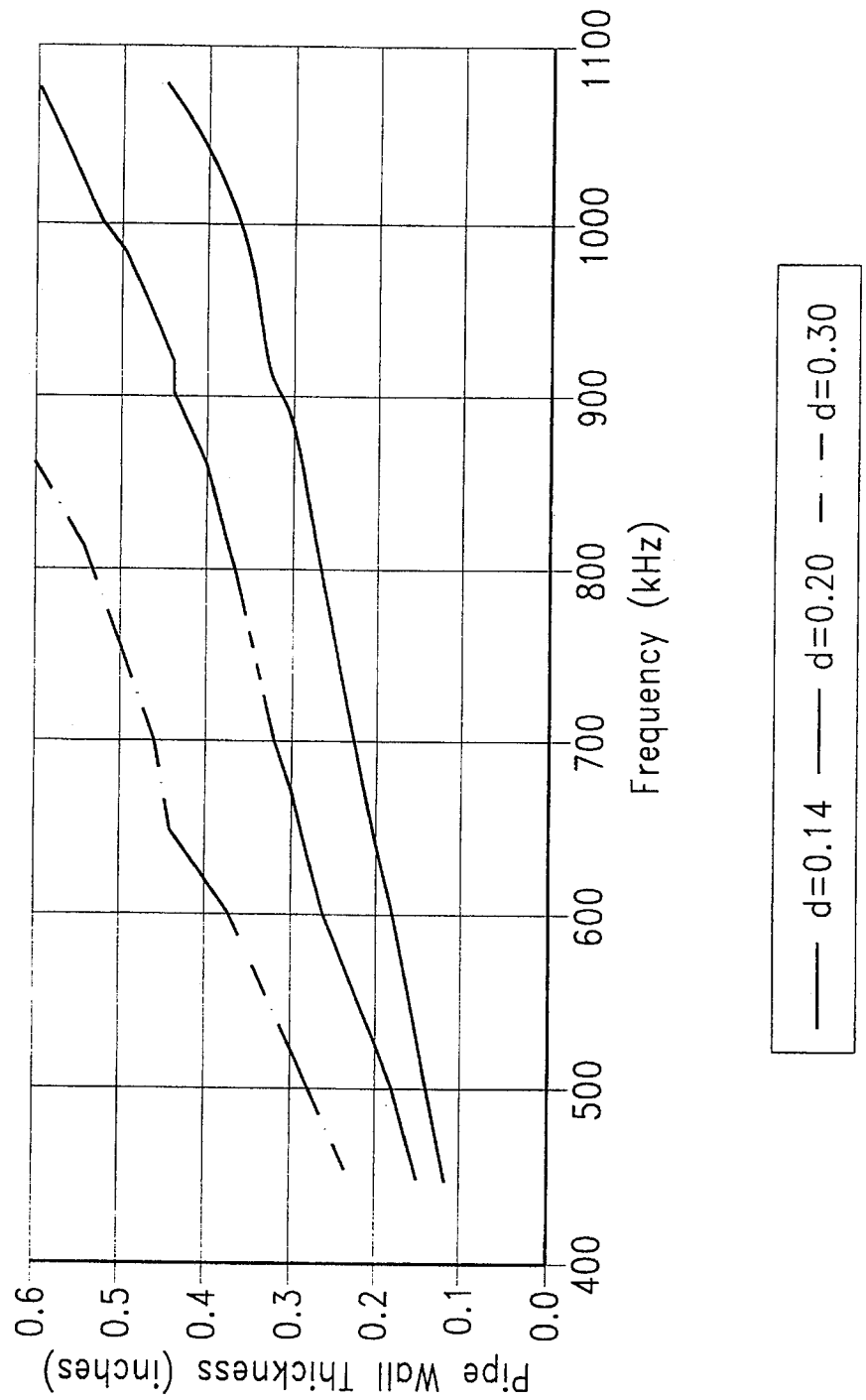
FIG. 9 is a chart for Lamb Wave frequencies vs. coil wire spacing for various material thickness.
Figure 10:
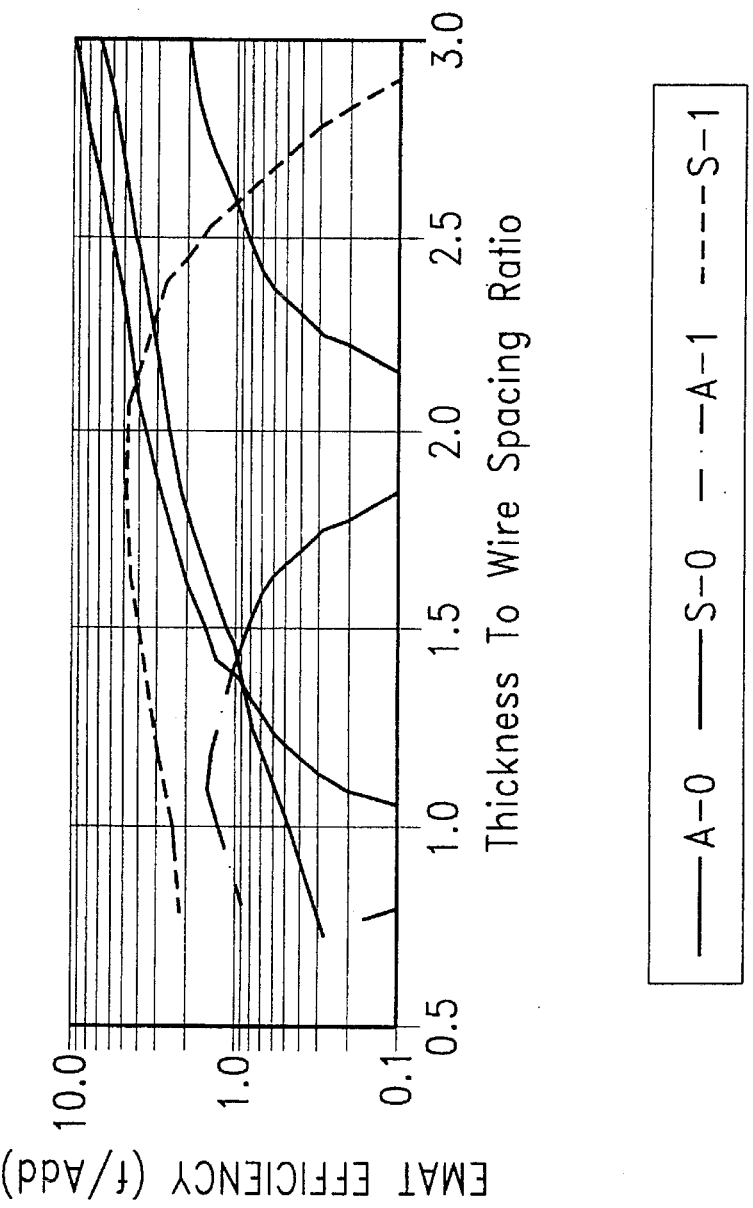
FIG. 10 is a chart for lamb wave efficiencies with various T/d ratios.

When different wall thicknesses are encountered in the field, Table 1, above, provides some guidance concerning the relationship between the transmitter and receiver coil wire 44a, 44b spacing, "d", (table 1) for the optimum EMAT coil to be used. In general, the ratio of the wall thickness to coil wire, spacing dimension (the T/d ratio) determines the frequency at which the EMAT must be tuned in order to excite and detect the particular wave needed for the inspection. If we choose to use the Symmetric n=1 mode, the frequency of operation can be calculated as a function of thickness or the three choices of wire spacings built into the EMAT coils listed above. This graph is shown in FIG. 9 and should be used to estimate the frequency for a given wall thickness and EMAT coil with a particular coil wire 44 loop spacing (d).

It has also been found that an increase in efficiency can be achieved by increasing the number of turns in the EMAT coils 44 or simply by increasing the electrical field strength. The use of Neodymium-iron-boron alloy for the magnets 27,28 has proven that such magnets can deliver 4 to 5 thousand gauss (0.4 to 0.5 tesla) to an EMAT coil 44 in a very confined space. For even higher field strengths electromagnets driven by high, pulsed currents have been used. However, some sacrifice in size is required.

The EMAT probe or scanner unit comprises both the transducer unit, housing the permanent magnets 27,28, the transmitter and the receiver coils 44a, 44b, and the carriage unit 2. The carriage unit central body houses the impedance matching network circuit and the preamplifier circuit 20,21. The impedance matching network 20 is a transformer that matches a Matec power amplifier 70 located in the remote control chassis 71, to the one or two ohm impedance of the EMAT coils 44. This tuned transformer and its tuning capacitor may need to be changed if the frequency of operation is expected to be beyond the frequency normally supplied with the unit. The preamplifier 21 is provided to aid in signal noise reduction. It has its own 110 volt AC power line but has no tuning or matching networks due to its broad bandwidth. A potentiometer mounted to the printed circuit board controls the gain of this amplifier. The EMAT carriage 2 is mounted on magnetized wheels 14, as shown in FIGS. 1–4, driven by remotely operated synchronous motors 16 at the Control Chassis 71 so that the carriage 2 can be driven externally along a pipe or plate during the inspection process. Both speed and direction of the motors 16 can be remotely controlled. It should be noted that the permanent magnets 27,28 built into the EMATs are very powerful and should be treated with respect. The entire probe unit 2 with its EMATS 4 or 8 may be removed from a pipe or tank 6,7 by simply twisting the unit 2 sideways until it is crosswise of the pipe's axis then lifted off. To remove from a large, flatter surface such as large tanks 7 the articulated frame 12 should be allowed to fold by removing the cross brace, thus allowing the entire unit 2 to be lifted, breaking the magnetic field by leveraging from the side of the wheels 14.

Figure 14:
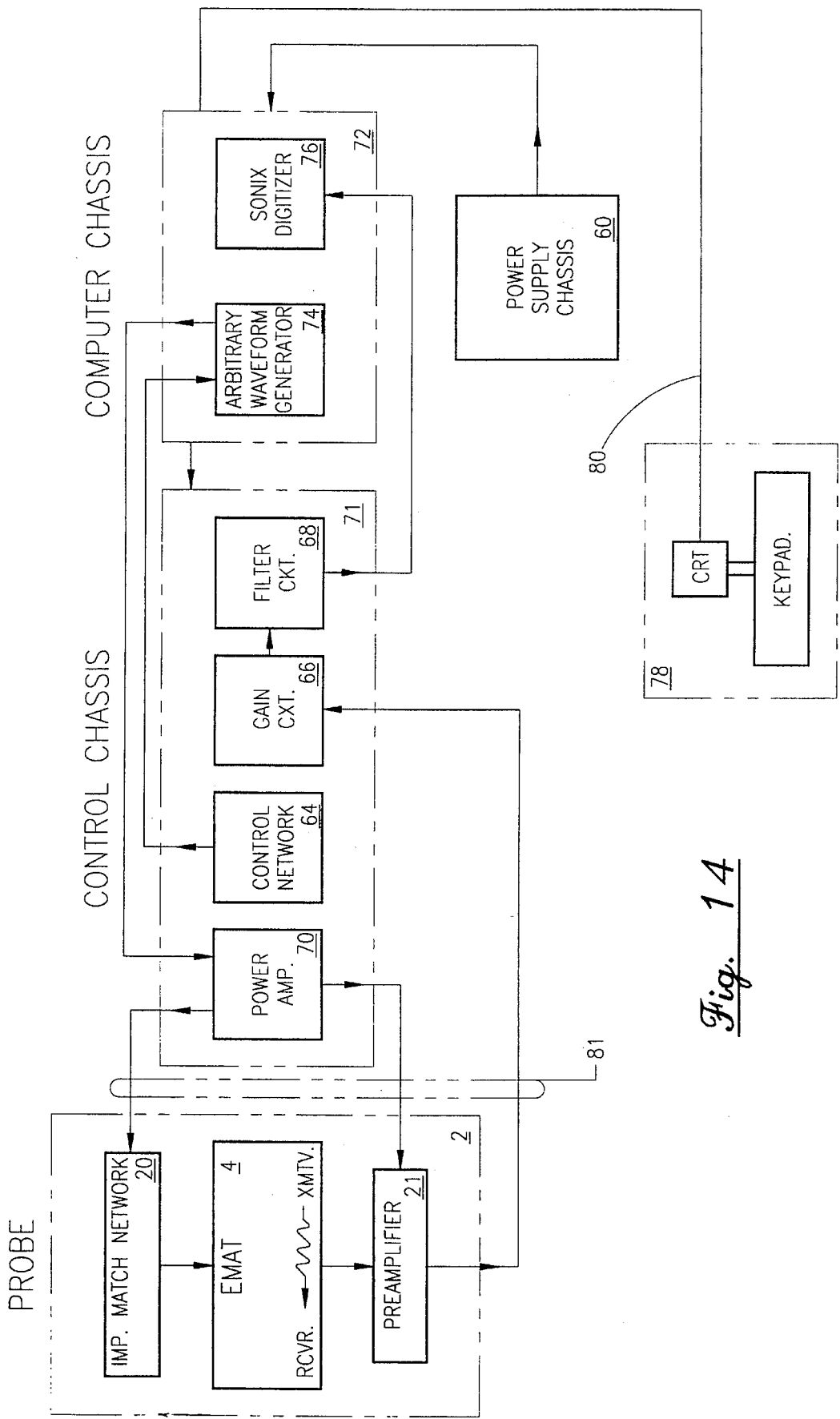
FIG. 14 is a block diagram of the essential electrical elements of the invention.

In addition to the carriage assembly 2 which carries the EMATs 4 or 8, some additional instrumentation is required. This instrumentation comprises three main chassis 71,72,78 and some support elements that serve as input/output units. These parts are displayed in the block diagram shown in FIG. 14, and their functions are described below.

a. Besides supplying AC voltages to the system the power supply chassis 60 also converts 120 volt AC into the various DC voltages required by the system. Each DC voltage is fused separately and a pilot light on the front panel shows that voltage is available and the fuse is good if the light is on. Fuses are accessible on the back panel.

b. The control chassis 71 contains three printed circuit boards; the control network 64, a gain circuit card 66, a filter circuit 68, and the Matec power amplifier 70 that supplies the high current tone burst to the EMAT transmitter coils 44(a).

c. The computer chassis 72 is a 486 personal computer with a built in math co-processor chip and a 65 megabyte hard disc. It also has slots for 5¼ and 3½ inch floppy discs so that data from particular inspections can be stored individually. The expansion slots for this computer hold an arbitrary wave form generator board 74 and an I/O board for producing the tone burst for the power amplifier plus a fast A/D board 76 for digitizing the RF signals coming from the EMAT receiver coil's 44(b) preamplifier 21.

d. The CRT display and keyboard 78 are connected to the computer through a 50 foot long umbilical cord 80 so that the display and controls can be accessible to an operator at a considerable distance from the instrumentation which may be housed in a trailer or in a van type vehicle.

Another umbilical cord 81 usually connects the control chassis 62 to the EMAT probe 2. However, it is well known that the probe 2 and its EMATs could be operated equally as well by wireless communication.

The methods used for inspecting pipe with the EMAT probe 2 are as follows:

A. SINGLE TRANSDUCER CASE

Conventional, ultrasonic testing relies on the measurement of the transit time of a high frequency sound pulse sent through the pipe directly under the transducer to measure the local wall thickness. Localized defects are usually detected by inducing sound waves at an angle to the surface and observing the echoes that are reflected by nearby discontinuities. The present invention utilizing EMATs 4 or 8, on the other hand, are particularly well suited for inducing low frequency waves which travel long distances from the transducer and hence inspect more material with each firing of the transmitter. The most effective of these special waves are the Lamb Waves with frequencies normally below one megahertz. However, in certain situations other waves can be utilized to gain the desired result. In any case the time of flight measurements are used to deduce thickness variations, and echo reflections are used to detect localized flaws.

However, because the EMAT'S 4 or 8 coupling to the pipe wall 6 is by electromagnetic induction without liquid couplant layers, signal amplitude measurements are more reliable; and the amplitude of the ultrasonic signals reaching a receiver can be used to betray the presence of defects that scatter energy from a sound beam which connects a transmitter with a receiver. This latter feature allows the detection of flaws oriented in any direction and is not limited to those flaw geometries that will reflect sound back to a particular receiving transducer.

Figure 17:
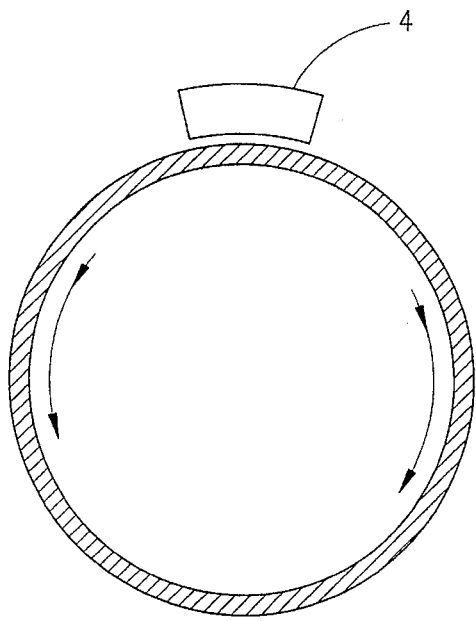
FIG. 17 is a simplified illustration of a single EMAT probe technique for inspecting a pipe.
Figure 18:
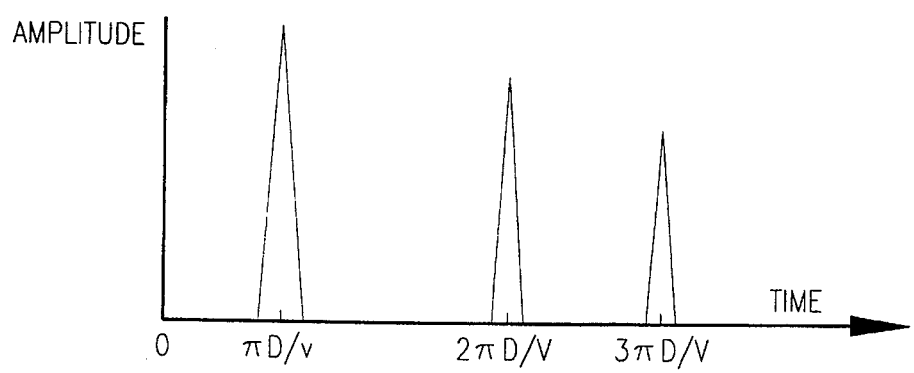
FIG. 18 is a graph indicating signal amplitude vs. time display as it would appear on an oscilloscope.

FIG. 17 shows the pipe 6 and EMAT inspection geometry that is the most simple to implement and which gives 100% coverage of a circumferential belt around the pipe. Thus, as the transducer is scanned along the length of the pipe, the entire pipe gets covered and all detectable flaws can be found at a scanning speed determined by the rate at which the transducer is moved. This speed can easily be in the range of a few feet per second. As seen in FIG. 17, only one EMAT 4 or 8 is shown because one magnet 27, or 28 and coil unit 44 can act as both a transmitter and receiver 44a, 44b. The EMAT launches sound waves both to the right and left; therefore, a clockwise and a counterclockwise rotating pulse of ultrasonic energy moves around the pipe circumference. These waves return to the transmitter/receiver coils after a time given by the equation $$\tau = \pi D / V \qquad \text{Equation (1)}$$

where D is the pipe diameter and V is the velocity of the wave form used. FIG. 18 shows the appearance of an oscilloscope arranged to display the amplitude of signals received from the EMAT 4 as a function of time after triggering the transmitter. Signals appear at integral multiples of the time given in Equation (1) above as the sound wave makes multiple trips around the pipe circumference. The oscilloscope display, shown in FIG. 18, can be used in the following three ways to detect flaws in the circumferential path followed by the sound beam:

1. the time of arrival of a signal;
2. the amplitude of a signal; and
3. the appearance of echo signals in the time interval between each round trip signal.

1. The Arrival Time Inspection Method For Lamb Waves, the velocity V in Equation (1) depends on the frequency of the ultrasonic wave, the construction of the EMAT's coil 44 and the thickness of the pipe 6 or tank wall 7. It is this thickness dependence that allows thin spots anywhere along the circumferential belt to be detected. In particular, if there is a part of the circumference that is thinner by an amount Delta-T extending over a distance "s," the time to traverse the circumference given in Equation (1) will change to $$\tau + \Delta\tau = (\pi D - s)/V + s/V' \qquad \text{Equation (2)}$$

where V is the wave speed in the normal pipe or tank plate wall thickness T, and V' is the wave speed in the thin section of thickness T–ΔT. From the theory of Lamb Waves and differential calculus, it can be shown that the relative shift in arrival time $\Delta\tau/\tau$ can be written $$\Delta\tau/\tau = -(m/M)C \qquad \text{Equation (3)}$$

where "m" is the mass of material missing at the thin spot. "M" is the total mass of the wall interrogated by the sound beam (i.e., the pipe material density times the pipe circumference times the transducer width times the pipe wall thickness. "T" is the wall thickness, and "C" is a theoretical coefficient that measures the sensitivity of the Lamb Wave velocity to changes in thickness. (That is, C=(T/V)(dV/dT) which is the slope of the sound velocity versus thickness curve.) By observing shifts in the arrival time of a zero crossing within an ultrasonic signal, very small changes in arrival time can be measured quite accurately and thin spots anywhere along the sound path can thus be detected. It is possible to measure Δτ to an accuracy better than 0.1 μsec, and τ is usually more than 10 μsec; so an (m/M)c of 1% is easily detected. Since Lamb Wave theory gives "C" equal to about –½, a thin spot that decreases the wall thickness by 20% over 10% of the circumference can easily be measured. Such a dispersed thinning will not cause an echo in a conventional, angle beam, shear wave, inspection and can be detected by an ultrasonic thickness gage only if the transducer is placed directly over the thin spot.

2. The Signal Amplitude Method. If the flaw is not a gradual thinning of the wall but is a crack or very localized corrosion pit, it can be expected to scatter or reflect some of the ultrasonic energy falling on it. This reflected energy can go in any direction, so the EMAT will probably not detect it as an echo. However, the energy passing through the flawed region will be diminished and the signal arriving at the receiver coil 44b after one or more trips around the pipe will be reduced. By monitoring the amplitude of the signals as the EMAT is scanned along the pipe, localized decreases in amplitude can be detected and used to locate flaws. This technique does not locate precisely where on the circumference of the pipe to look for the flaw, but instead, it tells the operator that a flaw exists at a certain location along the pipe length where additional inspections can then be concentrated. The sensitivity to small pits or cracks can only be determined by experience gained by comparisons of scans with various defects, and it is limited by the normal variations of the amplitude as the EMAT is scanned along nominal, flaw free samples of pipe. Because no compliant fluid is used and the EMATs are constructed to maintain a constant air gap between the coil and the surface due to the wheels 30 or 32, variations in the signal amplitude are usually very small during scanning along uniform, flaw-free pipes.

3. The Echo Method. If the flaws are good reflectors of ultrasonic energy such as cracks or the sharp edges of corrosion pits and if such flaws are oriented in a manner which reflects energy back along the acoustic path to the receiver coil 44b, then the receiver will detect an echo signal that arrives at a time different from that predicted by Equation (1). If an electronic window on the computer 78 is placed in between the round trip signals shown in FIG. 18, these echoes can be detected and used as a very sensitive indicator of the presence of a flaw. Unfortunately, the round trip signals themselves take up space along the time axis, so there are cases when small echoes will be obscured by the round trip signals. These lost times correspond to flaws located under the EMAT 4 or 8 and at the 180 degree locations opposite to the EMAT 4 or 8. By adding more EMATs, in particular at the 90 degree locations, these blind spots can be covered If one analyzes the times at which to expect the echo signals, it can be shown that two echoes should be seen for each defect. These correspond to separate reflections produced by the clockwise and counterclockwise propagating acoustic energy. A detailed analysis shows that the times of arrival of the echoes will always be exactly the same relative to the round trip signals, and echoes from multiple trips of energy around the pipe will superimpose perfectly on one another to make the echo signals appearing after "n" trips around the pipe, "n" times bigger. This phenomena can make the echo method extremely sensitive (but only to longitudinally oriented reflectors).

B. TWO TRANSDUCER CASE

Figure 15:
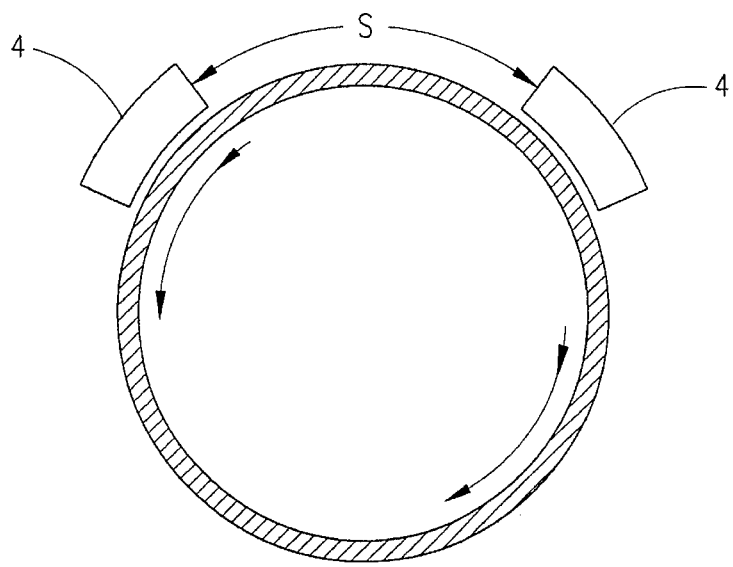
FIG. 15 is a simplified illustration of a two EMAT probe technique for inspecting pipe.
Figure 16:
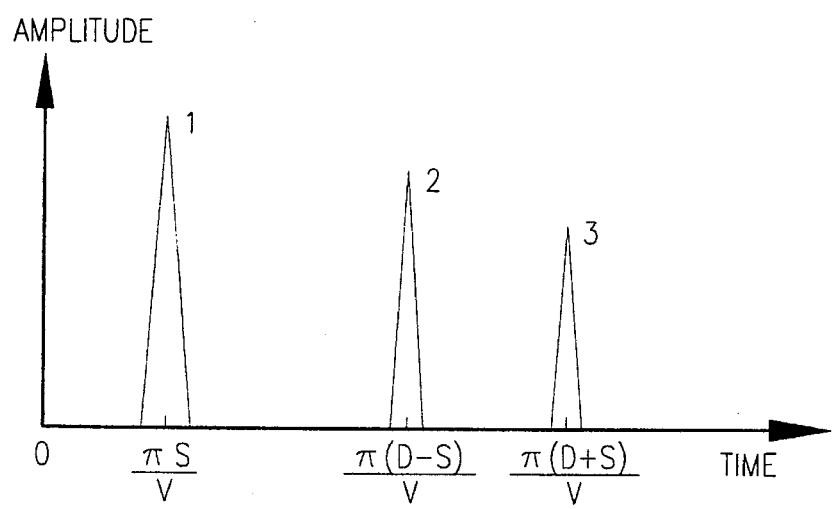
FIG. 16 is graph indicating signal amplitude vs. time display as it would appear on an oscilloscope.

The inspection method depicted in FIG. 15 is well suited to small diameter, very uniform pipes such as seamless tubing. For ERW pipe, the longitudinal weld line can introduce a wall thickening that shifts the transit time of the sound waves around the pipe and introduces localized reflectors that attenuate the signals and produce echo signals that appear like flaws. Since the weld is long and longitudinally oriented, very small variations in its geometrical characteristics produce strong, flaw-like indications. To overcome these problems, the transmitter and receiver can be separated and mounted on the pipe as shown in FIG. 15 or by simply electrically cross connecting the transmitter coil in one EMAT with the receiver coil in another EMAT. Such a configuration will produce the signal pattern shown in FIG. 16 in which two round trip signals appear that arrive before and after where the round trip signal would have appeared in a single transducer inspection case. If the transmitter and receiver are separated by a distance "S" (an angular separation of S/R where "R" is the pipe radius), the arrival times of the signals are:

t1 = S/v (signal #1)
   = the time of travel directly between transmitter and receiver
t2 = (πD − S)/V (signal #2)
   = the time for the counterclockwise signal to reach the receiver
t3 = (πD + S)/V (signal #3)
   = the time for the clockwise signal to reach the receiver Monitoring the time of arrival and the amplitude of these signals allows the short section of pipe located between the EMATs to be inspected separately from the balance of the pipe circumference. Thus, the weld line can be inspected separately from the rest of the pipe. The following three modes of inspection are now possible.

Mode 1, Monitoring Signal 2. Measuring the arrival time and amplitude of Signal #2 provides an inspection of all the pipe circumference outside of the space between the EMATs because this signal has traversed the long counterclockwise path between transmitter and receiver coils 44a, 44b. If the weld line is not in this path the signals should be constant and appear like those found in a flaw free section of seamless tubing.

Mode 2. Monitoring. Signal 3. Measuring the arrival time of Signal #3 by itself gives information on the full circumference of the pipe with extra emphasis on the small region of length "S" that lies between the EMAT'S because Signal #3 has traversed this short section twice. If the transducers are positioned to straddle the weld line of an ERW pipe, Signal #3 will be dominated by the quality of the weld. In particular, changes in the arrival time of Signal #3 that are not in Signal #2 can be immediately interpreted as variations in the thickness at the weld caused by poor trimming of the weld flash during manufacture of the pipe. Similarly, variations in the amplitude of Signal #3 that are not in Signal #2 can be ascribed to reflecting defects in the weld. Thus, comparing Signals #2 and #3 leads to a concentrated inspection of the small section of pipe between the transducers.

Mode 3. Combining Signals #2 and #3. If the ratio of the amplitudes of Signals 2 and 3 are formed, the resulting quantity measures the attenuation of the sound wave that has passed through the distance "S" twice and is, therefore, able to detect the scattering of energy by defects in this small section of pipe. Likewise, the ratio of the two times of arrival can be related to time shifts caused by flaws that lie in the space "S." Thus, the two ratios provide a sensitive inspection of the section of pipe marked by the length "S" in FIG. 15. By scanning the length of a pipe with the EMAT paired and located at different angular locations relative to the top of the pipe/ a very detailed and sensitive map of the flaws in the pipe can be developed.

In order to relate the ratio of transit times to the mass of material missing in a flaw (the quantity "m" in Equation 3), we let t(2) be the time of arrival of Signal #2 and t(3) be the arrival time of Signal #3. The difference in arrival times between t(3)−t(2), can be related to the ratio of arrival times, t(3)/t(2) through the equation:

$$t(3)-t(2)=t(2)\{[t(3)/t(2)]-1\}=2S/V \qquad \text{Equation (4)}$$

or $$t(3)/t(2)=2S/Vt(2)+1 \qquad \text{Equation (5)}$$

where "S" is the separation distance of the EMATs, and the factor of 2 appears because Signal #3 has traversed the distance "S" twice. If there is a flaw in the distance "S" whose length is "s" and in which the velocity of sound is V', the right side of Equation 4. becomes;

$$2(S-s)/V+2s/V'=(2S/V)[1-(m/M)C]=t'(3)/t(2) \qquad \text{Equation (6)}$$

where t'(3) is the arrival time of Signal #3 when a flaw is present, and "M" is now the mass of material between the EMATs. Subtracting Equation 6 from Equation 5 yields the change in the transit time ratio which can easily be graphed as a function of the distance along the pipe to expose the localized variations that an operator or alarm system can recognize as a flaw.

Equation (7)
Change in transit time ratio = $[t(3) - t'(3)]/t(2) = [2S/Vt(2)][Cm/M]$ from which the severity of the flaw as measured by m/M can be deduced since the distance between transducers "S", the sound velocity "V", the arrival time of the second signal t(2), and the sensitivity coefficient "C" are all known for a given inspection case.

Although the Lamb Wave discussed above is the most often used wave form for the EMATS, several alternative embodiments of the EMAT probe sensor capable of exciting and detecting other ultrasonic wave forms in metal parts and structures have been researched and used successfully for particular inspection problems. The list and discussion below is indicative of some of the special circumstances which may be encountered in detecting a specific flaw in a given material.

SHEAR WAVE transducers launch and detect ultrasonic shear waves perpendicular to the surface of the part similar to conventional transducers; however, they are configured with an elongated spiral coil sandwiched between the face of the magnet and the part being inspected.

ANGLE BEAM transducers launch and detect either shear or longitudinal waves at an angle to the surface. The EMATs utilize either tangential magnetic fields, produced by a pulsed electromagnet, or permanent magnets placed directly over the EMAT coil. The angle is controlled by the design of the coil and the frequency of operation. Maximum efficiency can be exploited if the shear wave is placed at a 30-degree angle to the surface.

RAYLEIGH OR SURFACE WAVES work well with the EMATs as a result of their ability to function without a compliant to dampen the surface wave. These wave forms have proven to be excellent for inspecting metal surfaces for laps, seems, cracks and pits. It has been found that EMATs which excite and detect these waves are a special application of the angle beam transducer whereby the angle of incidence is 90-degrees to the surface.

LAMB WAVES are generally used where the thickness of the metal is comparable with the wavelength of the sound wave. In such cases the Lamb wave form is in resonant mode with the sheet and exists only at a specific wavelength and frequency for a given material thickness. By choosing a drive frequency to match the design of the EMATs coils 44, a very efficient transduction can be achieved for a selected Lamb Wave with properties suitable for any particular inspection problem.

SHEAR HORIZONTAL WAVE transducers are shear waves with their polarization direction parallel to the surface of the part under inspection. This type wave form, seldom suffers from mode conversion, therefore, its echo patterns are clean and easily interpreted. To use this type wave form the EMAT is constructed of a simple elongated spiral coil and an array of small permanent magnets 28.

HIGH TEMPERATURE EMATs have been developed by encapsulating the EMAT in a water cooled chamber and constructing the coils 44 using ceramic insulated wire. EMATs can be constructed for use in environments with temperatures above 2000 degrees Fahrenheit. Provided the intrinsic attenuation of sound in the hot metal is not excessive, any of the EMAT types discussed above can be used in this manner.

FOCUSING EMATs have been developed by bending the wires of EMAT's 4 or 8 coils 44 in a manner which allows the waves to be focused on a particular location, either on the surface or below the surface of the part being inspected.

OPERATION

Figure 19:
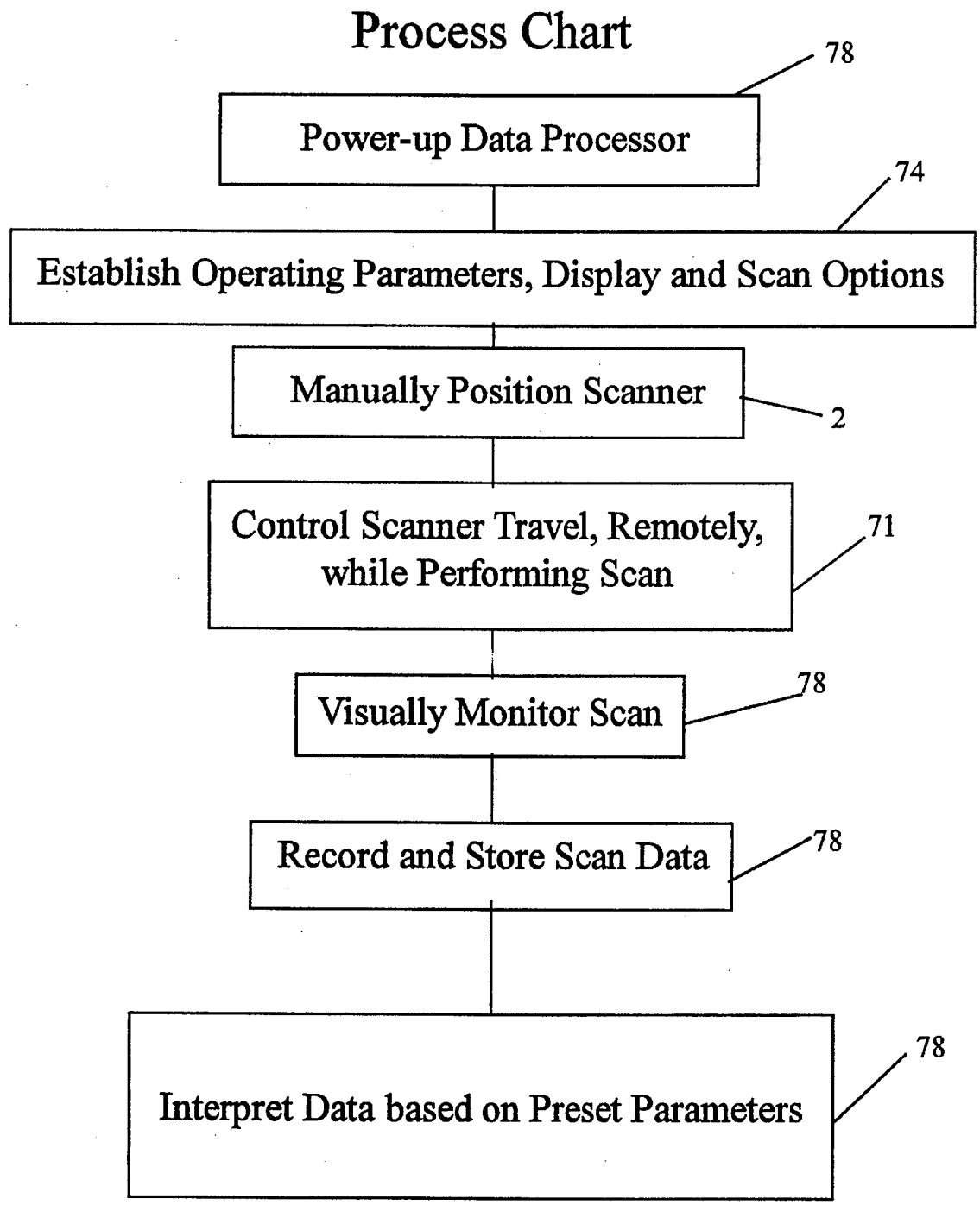
FIG. 19 is a process chart.

The process chart FIG. 19 outlines the following set up and operation procedures.

To put the system into operation, turn on the computer using its power switch at the bottom center of the computer chassis 72. Power is supplied by the power chassis 60. This should bring up a menu on the CRT 78 with CALIBRATE SYSTEM accentuated. Next press the power switch on the front panel of the power supply chassis 60. This should illuminate the row of pilot lights that indicate the availability of DC power for the instrumentation as well as illuminate the active light on the front of the control chassis 71. With all these pilot lights on, the system is ready to operate and is waiting for an initiate pulse from the computer. This initiation signal is produced only after calibration is complete.

To shut the system down, move the cursor on the CRT 78 to EXIT and follow the instructions that appear as menus when the ENTER key is pressed.

Calibration is achieved with all the pilot lights illuminated and the CRT 78 high lighting CALIBRATE SYSTEM. Press the ENTER key to bring up a menu under the CALIBRATE SYSTEM heading. Its first two entries, entitled "Fine Tune Windows," will display the RF ultrasonic signal that the computer will process. However, we must set the arbitrary wave form generator (AWG) 74 and define the windows we desire before viewing this signal. Use the arrow keys to move to "create TB." This allows the parameters that control the tone burst (TB) to be established.

Define which TB—use 1. (Choices 2, 3 and 4 are not used here.) Tone burst frequency—choose 800 khz or what is read from the tone burst amplitude—choose 0.6 (sets the initial drive level for the Matec transmitter)

Number of Cycles—between 5 and 10 is good for a start . Sets the number of cycles in the tone burst.

Transmitter Gate—gives the time duration of the tone burst as calculated by the computer from the frequency and the number of cycles. You have no choice.

Main Bang Blank—Choose the number of microseconds to keep the pre-amp off in order to keep the transmitter power out of the receiver. Should be larger than the Transmitter Gate but less than the arrival time of the first round trip signal.

Start Gains and End Gains—Not used here. (Allows for a kind of distance amplitude correction at early times.) Keep the entries less than Main Bang Blanking.

Press Y for yes—System returns to CALIBRATE SYSTEM.

Press ENTER and use arrow key to select DEFINE WINDOWS. This choice allows the operator to set windows around two signals for measuring the time of arrival and amplitudes of two signals.

Str. Channel to use—Enter 1 (Channels 2, 3 and 4 not used here.)

TOA A/D Sampling Rate—This sets the digitalization frequency to be used on the signals. Choose 25 kHz in order to have a 0.04 μsec interval between data points. This assures the minimum accuracy for measuring the Time of arrival (TOA).

Waves to Avg—This number sets the number of wave forms that are averaged together to improve the signal-to-noise ratio. It should be set between three and ten.

For the First window:—The number of microseconds to delay the start of the display of the RF signal and the first window. This is like the delayed sweep control of an oscilloscope. This time delay can be estimated by calculating the circumference of the pipe (π times the diameter) and dividing by the sound velocity of the Lamb Wave mode (0.19 in/μsec) and then subtracting 10 or 20 μsec to start the "sweep" ahead of the signal.

Start Xing window at—The number of microseconds at which a small window that brackets a zero crossing in the middle of the signal will appear. The time of arrival (TOA) of this zero crossing is what the computer will use as the arrival time of the first signal. This number should be smaller than half a cycle of the RF frequency being used, i.e. less than 0.6 μsec for an 800 kHz signal.

Size of Ampl Win1—The number of microseconds that the first window will be open. It should be about 20 μsec and bracket the maximum of the RF signal. The computer will center it around the zero crossing window chosen above.

Size of the LSF Win1—The computer can calculate the exact zero crossing time by a Least Squares Fit (LSF) technique, but this program is not used here. this value at 0.4 μsec.

Tracking Window 1—The computer will keep the zero crossing centered in the zero xing window if you answer yes here (which you should do).

For Second Window—These choices set the second window parameters and use the same instructions as above except the offset and the start xing win2 are delayed by the amount of time between the first and second signals. This is usually about ¼ of the circumferential transit time calculated above.

For info Only—The computer converts the times you have chosen above into the number of digitalization time intervals using your choice of A/D sampling rate. It then converts the number back into µsec and displays it here. Answer YES to set the values chosen into the computer and return to the CALIBRATE SYSTEM menu.

Press RETURN to bring up FINE TUNE WINDOW NO. 1. Press RETURN and the CRT will activate the transmitter, and the CRT will display the first RF signal using the timing parameters chosen above. Since these choices were approximate, the following key strokes can be used to fine tune the windows and the signals; so they are optimized for making a pipe inspection. These key strokes are described in the HELP window which is available by pressing F1. To better position the signal on the screen:

Page Up increases the start of the time axis by 10 µsec.

Page Down decreases the time axis start by 10 µsec.

To control the size of the signal:

Cap. B—bumps the amplifier gain upward (and increases the noise

Lower case b—bumps the gain down.

Cap V—increases the drive of the transmitter power amplifier and makes the signal larger up to the limit of the amplifier! Use "V" key to increase the signal (without increasing the noise) until the signal no longer increases with each pressing of the key and then lower the drive by pressing the lower case "v" key until the signal drops slightly.

Lower case v—decreases the drive to the amplifier. The signal in the first window should be adjusted to cover about 90% of the vertical display.

Cap C—increases the number of cycles in the signal. It will make the signal a little bigger and a lot longer and is best chosen to be as short as possible without sacrificing signal strength.

Lower case c—decreases the number of cycles in the signal.

Cap F—increases the frequency of the drive signal and is used to optimize the tuning of the Lamb Wave for the particular pipe being tested.

Lower case f—decreases the frequency. F and f should be used to obtain a large, bell shaped envelope for the signal.

Fine tune the window:

Arrow left—moves the smaller zero crossing window to the left.

Adjust it to bracket a zero crossing near the center or largest cycle in the signal.

Arrow right—moves the zero crossing window to later times.

F4 redraws the screen to eliminate dashed lines left behind by old window settings.

When the signal in Window 1 is optimized and the windows are properly positioned, hit ESC and return to the CALIBRATE SYSTEM menu. Hit ENTER twice to choose Fine Tune 2 Windows and then ENTER again to display Window 2.

Use B,b, V,v and F, f very little to optimize the second signal because these adjustments also effect the first signal which has just been optimized. (Physics and the computer will insist that the second signal be smaller than the first. On rare occasions, an adjustment of the frequency may be needed to insure that this size relation is true.) Use the arrow keys to adjust the zero closing window to a large cycle in the center of the second signal.

The system is now set and ready to run on a particular pipe. If the system is exited or if there is a power failure at this point, the window and gain settings so carefully established by the procedures described above will be lost and must be redetermined. To insure these settings, return to the CALIBRATE SYSTEM menu and use the CHANGE SYS. CONFIG., LOAD CONFIG. and WRITE CONFIG. instructions to give the particular configuration developed above a name and memory location, so they can be recalled and used whenever desired.

C. Do Run. To inspect a pipe, use the arrow keys to move the cursor from CALIBRATE SYSTEM to DO RUNS. Pressing ENTER brings up two choices; (1) Window Run and (2) Window Run. These choices refer to the single and dual transducer options discussed herein. 1 window Run—processes and graphs the measurements obtained with one EMAT acting as a transmitter and as a receiver. Thus, it inspects the entire circumference from one probe. Pressing ENTER initiates an inspection run and brings up two coordinate systems on the CRT. The top coordinate system plots the maximum signal amplitude found in the window selected as the first window of the DEFINE WINDOWS menu and graphs it as a function of measurement number. There are 512 measurements across the screen. Thus, the rate of measurement, and hence, the rate at which the data points appear to scan across the screen depends on the Pulse Repetition Frequency and the number of averages chosen in the Define Windows menu.

The Pulse Repetition Frequency is controlled by a screw driver adjustment on the rear panel of the control chassis. It is usually set at 50 Hz or a transmitter firing every 0.02 sec. If only 3 averages are used, it takes 0.06 sec. to record one measurement and, therefore, only 30 sec. to collect 512 measurements and cross the CRT display. If 10 averages are used, it takes 102 seconds to cross the screen. At a scan speed of 1 foot/sec. the CRT would display 102 feet of pipe with a measurement every 2.4 inches. If 10 feet were scanned in 30 sec. with 3 averages per measurement, there would be a measurement every 0.25 inches. Since the EMAT is 1.5 inches wide, a point flaw would affect the signal for 6 measurements. As explained previously, a flaw appears as a localized dip in the amplitude versus probe location graph.

The lower coordinate system on the "Do Run" display plots the "Time Of Arrival" (TOA) of the signal in the first window as deduced from the zero crossing window chosen. A deviation from the normal time of arrival indicates a thickness variation somewhere in the circumferential belt being inspected. For the Lamb Wave "SI" mode, a thinning causes the wave to increase its velocity so a thin region will cause the transit time to decrease.

2 WINDOW RUN—This inspection technique is discussed in Section II-B where two EMATs separated by a short distance are scanned along the pipe. Here again two graphs are displayed as a function of measurement number, but now each graph has two lines, one for the signal in window #1 and the other for the signal in window #2. In the top graph, both amplitudes are displayed; and that graph associated with window #1 can be recognized because it has a larger signal amplitude. Both "Time of Arrival" graphs are plotted to start at zero in the center of the "Y" axis of the display. Thus, they can be distinguished only by color which is the same as used in the amplitude plots. If the second window graph deviates from the first window graph, it indicates that a flaw lies in the space between EMATs . Simultaneous delineations in both windows are to be interpreted as arising from flaws outside the space between transducers. At the end of a run, the graphs remain on the CRT for visual examination. To save and print the results of a run, press the ESC key, and menus will appear that allow the run to be labeled with an 8 character designation as well as a longer descriptor. The short label is used for recalling the run for further processing.

D. Graph Past Run. After a run has been stored, pressing the ESC key will return the operator to the CALIBRATE SYSTEM menu. Moving the cursor to GRAPH PAST RUN and pressing the ENTER key, brings up a menu that allows additional signal processing.

Graph 2 Window Run—presents a list of the 8 character titles assigned to the data taken on the previous runs using the two window technique. Moving the cursor to a particular run and pressing ENTER will present the amplitude and TOA graphs developed during that run. Pressing F2 will send the graphs to the printer for hard copy documentation.

Graph 2 Window Ratios—The raw data graphs developed during an inspection run are informative if studied by a skilled operator. However, to accentuate the variations that may be flaws, it is better to normalize the data by taking the ratios, described herein where the mathematical procedure is analyzed. Making the Graph 2 Window Run choice, presents the data as ratios of the amplitudes and arrival times which eliminates background variations and emphasizes the inspection of the space between the two transducers as described. Again, pressing F2 creates a hard copy print out of the 2 window data.

Graph 1 Window Run—presents the list of 8 character titles assigned to runs made with only one transducer. Choosing one brings up the data display generated by that run and allows it to be printed. The interpretation of this data is as discussed previously.

Save 1 Win Data to ASCII—transfers a particular single transducer run to an ASCII file where it is available for transfer into other data processing programs for mathematical manipulation and presentation in different formats.

E. EXIT. The last choice on the CALIBRATE SYSTEM menu is EXIT. Making this choice brings up menus to help the operator save whatever data desired and insures a safe shut down of the system.

CHOICE OF LAMB WAVE MODE

Three properties of Lamb Waves and the EMATs that excite them need to be considered in choosing a design for inspecting tubulars installed in refineries or the like are as follows: (i) the efficiency of the EMAT when operated under permanent magnets that apply the fields normal to the surface; (ii) the desire to minimize damping by any fluids that may be in the pipe; and (iii) minimizing the effect of dispersion on the apparent attenuation of the signal amplitudes.

1. The efficiency of an EMAT 4 or 8 in a normal magnetic field is proportional to the reciprocal of the admittance $Y_x$ which controls the displacements perpendicular to the magnetic field. Numerical values for these admittances are available from the calculations of Thompson and Gray. Papers published by Thompson show that the efficiency is proportional to $f/Ad^2$ where f=the frequency, "d" the wire spacing in the EMAT coils 44a, 44b and "A"=the admittance parameter calculated by Thompson and Gray. This efficiency coefficient is plotted in FIGS. 9–13 as a function of T/d for the first four LambWave modes. Clearly, the largest choice of modes with high efficiencies occurs near T/d=2. Thus, for wall thicknesses in the 0.2 to 0.5 inch range, the wire spacings will range from 0.1 to 0.25 inches for tubulars in the 0.5 to 1.0 inch wall thickness range for tanks the spacings will range from 0.250 to 0.600 inches either of which is quite acceptable.

2. To minimize damping by fluids in the pipes or tanks 6 or 7, it is important to choose wave displacements that are not perpendicular to the surface because such motion will launch compressional waves into the fluid. Therefore, modes are sought with large tangential displacements ($U_x$ large) and small normal displacements ($U_z$ small) which means that the admittances $Y_x$ should be small and $Y_z$ large. Examination of the admittance curves shows that $Y_z$ is infinite (the displacements are pure tangential) for the symmetrical n=1 mode (the S(1) mode) at T/d=1.31 and for the A1) and the S(O) modes at T/d=O. Combining this information with the efficiency plot indicates that the S(1) mode near T/d=1.3 will have a quite acceptable efficiency and will not couple to the liquid.

3. Dispersion losses arise where the wave velocity is very frequency dependent. This causes a pulse of energy to spread out in time and decrease its amplitude. Thompson and Gray have used this phenomenon to calculate the distance required for a pulse to spread so much that it has only half its original amplitude. For the S(1) mode, there is a sharp maximum in this travel distance at T/d=1.4 which is associated with a maximum in the group velocity. This maximum in group velocity extends over the range 1.3<T/d<1.6 which encompasses the purely tangential displacement point at T/d=1.3.

Therefore, we conclude that:

the Symmetric n=1 mode with 1.3<T/d<1.4 will give us high efficiency, low coupling to the fluid in the pipe and a minimal loss from dispersion.

Figure 11:
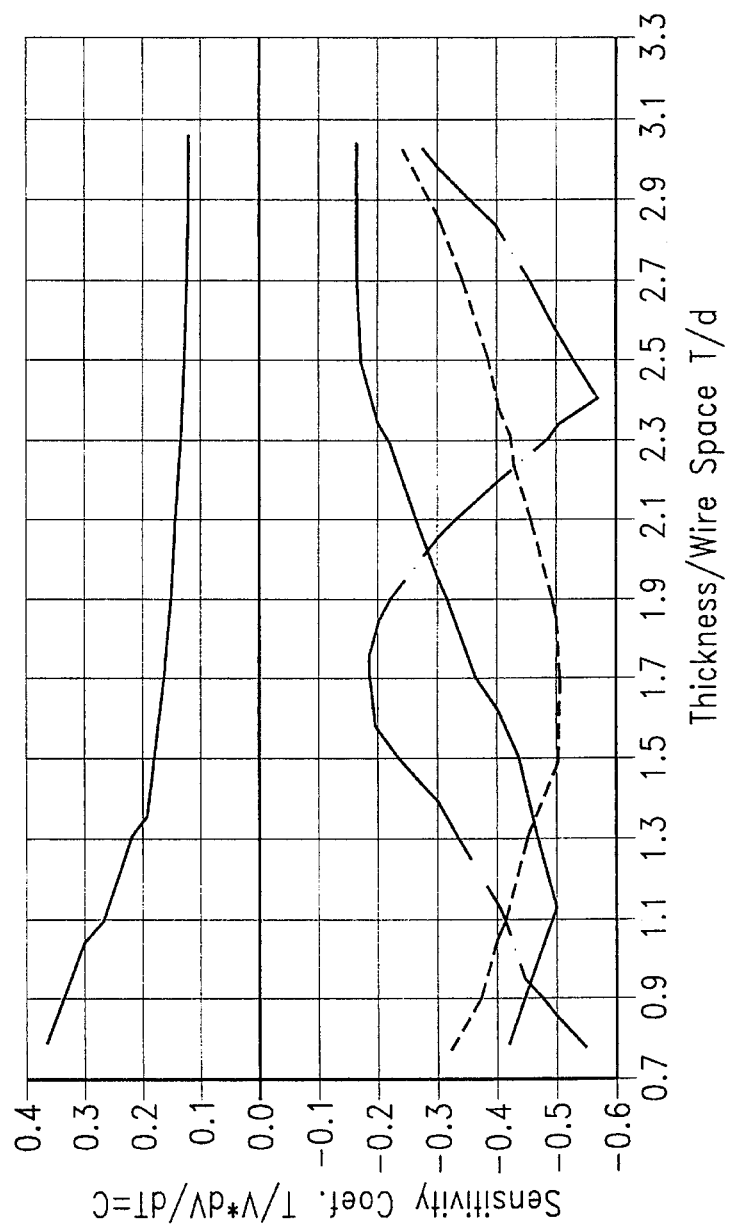
FIG. 11 is a chart showing thickness to coil wire spacings at various sensitivity coefficients.
Figure 12:
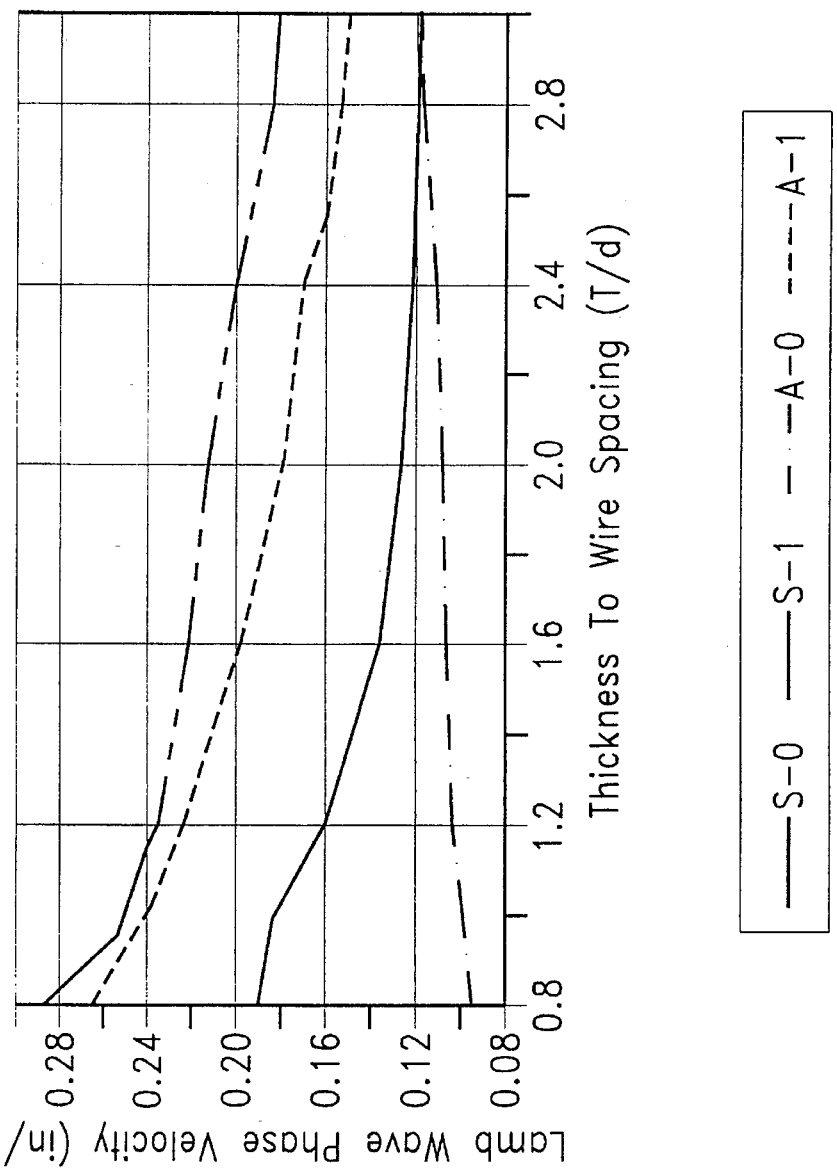
FIG. 12 is a chart showing lamb wave phase velocity with regard to wire spacing.
Figure 13:
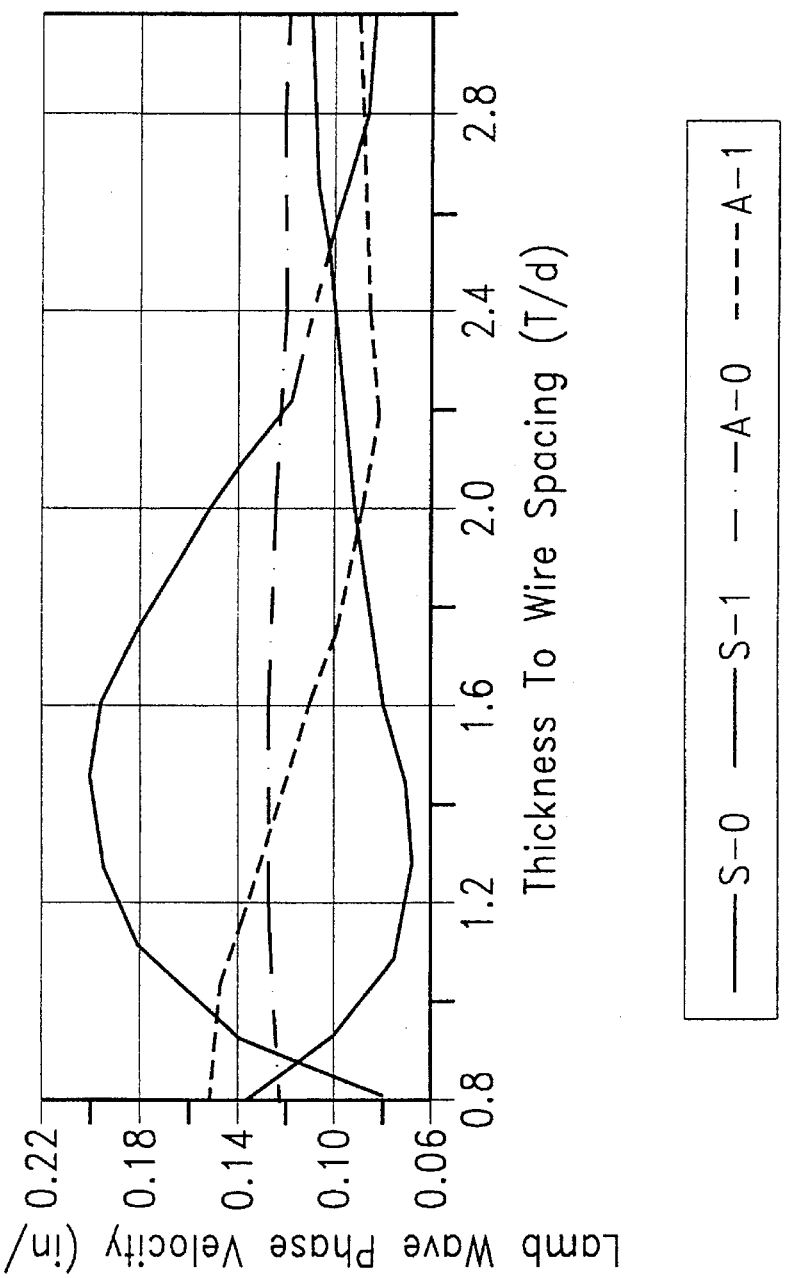
FIG. 13 is a second chart showing lamb wave phase velocity with regard to wire spacing.

The above conclusions may be illustrated by the graphs depicted in FIGS. 10–13. Wherein FIG. 10 indicates the relative efficiencies with which various Lamb wave modes are excited and detected as a function of the Pipe thickness to EMAT coil wire spacing; FIG. 11 depicts how sensitive the phase velocity of various Lamb wave modes are relative to thickness changes with the sensitivity coefficient shown unitless and proportional to the slop of the phase velocity versus thickness curves; FIG. 12 depicts the variation of the Lamb wave phase velocity with wall thickness to EMAT wire spacing ration (T/d), wherein the phase velocity is the speed that a phase feature such as a zero crossing moves through the material; and FIG. 13 depicts the variation of the Lamb wave group with wall thickness to EMAT wire spacing, (T/d), wherein the group velocity is the speed that a tone burst or RF pulse moves through a dispersive material.

Numerous variations and modification may be made without departing from the present invention. For example, structures other than pipes, such as tanks, can be inspected by the method and apparatus disclosed herein. In addition, it is obvious that the disclosed invention could be made stationary and the pipe passed across the EMAT probe. Accordingly, it should be understood that the form of the present invention disclosed herein and depicted by the associated drawings is illustrative only and is not intended to limit the scope of the invention.

What is claimed is:

1. A portable Electromagnetic Acoustic Transducer (EMAT) system for linear externally inspecting non-rotating ferrous tubulars and tanks for flaws and thinning, comprising:

a) a power supply;

b) a computer chassis electrically connected to said power supply;

c) a CRT and keypad electrically connected to said computer;

d) a control chassis electrically connected to said computer chassis;

e) at least one couplantless, self-propelled Electromagnetic Acoustic Transducer (EMAT) probe, having integral juxtaposed, convoluted transmitter and receiving coils, umbilically connected to said control chassis; and f) a software program, having predetermined parameters for comparison with data being received from said EMAT probe and thereby determining flaws and thinning while scanning a tubular or tank.

2. A portable Electromagnetic Acoustic Transducer (EMAT) system for externally inspecting ferrous tubulars and tanks for flaws and thinning according to claim 1 wherein said computer chassis further comprises:

a) a wave form generating means controlled by said control chassis, for producing a tone burst; and b) a digitizing means for digitizing RF signals emanating from the said EMAT probe.

3. A portable Electromagnetic Acoustic Transducer (EMAT) system for externally inspecting ferrous tubulars and tanks for flaws and thinning according to claim 2 wherein said control chassis further comprises:

a) a power amplifier for amplifying signals emanating from said wave form generator before sending said signals to said EMAT probe;

b) a control network for controlling said wave form generator;

c) a gain circuit card for receiving and processing signals being received from said EMAT probe; and d) a filter circuit for reducing noise in signals emanating from said gain circuit before transmission to said digitizer.

4. A portable Electromagnetic Acoustic Transducer (EMAT) system and probe apparatus for externally inspecting ferrous tubulars and tanks for flaws and thinning said EMAT probe apparatus comprising:

a) a carriage having a central body housing;

b) an adjustable articulated frame, centrally attached, perpendicular to said central body housing;

c) an Electromagnetic Acoustic Transducer vertically and horizontally adjustable, attached to the distal ends of said articulated frame; and d) a magnetic wheel disposed forwardly and in offset, rolling, alignment with each of said transducers.

5. The apparatus of claim 4 wherein said magnetic wheel is electrical motor driven.

6. The apparatus of claim 4 wherein said adjustable, articulated frame is adjustable between a first, flat position of 180 degrees, to a second inverted position having an included angle of approximately 90 degrees.

7. The apparatus of claim 6 wherein said Electromagnetic Acoustic Transducer and said magnetic wheel is secured to a moveable plate laterally adjustable incrementally along each end of said articulated frame.

8. The apparatus of claim 7 wherein said Electromagnetic Acoustic Transducer is further laterally adjustable within said moveable plate.

9. The apparatus of claim 8 wherein said EMAT is vertically adjustable with respect to said magnetic wheel.

10. The apparatus of claim 9 wherein said magnetic wheel motors are synchronous and controlled remotely.

11. The apparatus of claim 4 wherein said carriage's central body housing further comprises:

a) a preamplifier means for amplifying signals received from said EMATS;

b) a impedance matching network for correlating signal input to said EMATS from said control chassis; and c) electrical jack connections for connecting said EMATS to a control system.

12. The apparatus of claim 11 wherein said EMAT is comprised of:

a) a rolling carriage;

b) a permanent magnet housed within said carriage;

c) integrated transmitter and receiver coils, formed in an interposed relationship, located within the magnetic field of said magnet's north pole;

d) a wear plate covering said transceiver coils attached springably to said carriage; and e) an electrical jack for connecting said transmitter and receiver coils to said carriage system.

13. The apparatus of claim 12 wherein said wear plate is titanium.

14. The apparatus of claim 13 wherein only the north pole of said block magnet is exposed to said coils.

15. The apparatus of claim 14 wherein said EMAT coils serve as both transmitter and receiver.

16. The apparatus of claim 12 wherein said Electromagnetic Acoustic Transducer is further comprised of:

a) a central frame having upper, lower, fore and aft cavities therein;

b) a cover plate attached integrally within said central frame's upper cavity;

b) a magnet module having an exposed curved lower side located integrally within said central frame, attached to said cover plate;

c) a plurality of permanent, metal, slab, magnets retained between said cover plate and said module;

d) a wear plate attached to the exposed side of said module;

e) a plurality of coils adhered to said wear plate located between said wear plate and said module;

f) a plurality of wheels rotatably attached to said central frame; and g) an electrical connector attached to said coils, integrally attached within said central frame's fore or aft cavity.

17. The apparatus of claim 16 wherein said permanent magnet is comprised of individual metal slabs approximately, ⅛ inch by ½ inch by ½ inch deep arranged in pairs consisting of three rows of 12 slabs each.

18. The apparatus of claim 17 wherein said magnets are magnetized along the ½ inch dimension and arranged so as all north poles of said magnets are turned outward toward the material being inspected.

19. The apparatus of claim 18 wherein said magnets are Neodymium-Iron-Boron with an energy product of 35 MGO.

20. The apparatus of claim 19 wherein said coils comprise both transmitting and receiving coils with said transmitting coils interposed with said receiving coils in precise symmetrical loops.

21. The apparatus of claim 20 wherein said transmitting and receiving coil wire loop spacing is one-half the wave length.

22. The apparatus of claim 21 wherein the optimum ratio of material thickness to wire spacing for said transmitting and receiving coil wire loops is between 1.3 and 1.4.

23. The apparatus of claim 22 wherein said coils comprise both transmitter and receiver coils juxtaposed and interposed within each other in a manner which insures coinciding receiving and transmission points.

24. The apparatus of claim 12 wherein said Electromagnetic Acoustic Transducer comprises:
   a) a head block;
   b) a tail block bolted to said head block;
   c) a pair of side rails having bar clamps along their outer side and cavities formed therein bolted to said head and tail blocks;
   d) a block magnet disposed in a clamped relationship integral with said head, tail and side rails;
   e) a plurality of coils disposed along the exposed face of said block magnet, the ends of which extend into said side rail cavities culminating in electrical connections recessed into the ends of said side rails; and
   f) a wear sheet covering said coils and said block magnet springably secured to each of said side rails by said bar clamps.

25. An Electromagnetic Acoustic Transducer Probe as defined in claim 24 wherein said EMAT further comprises a plurality of beveled vee wheels attached to said head and tail blocks for maintaining a predetermined spacing between said blocks and the material being inspected.

26. The system and apparatus as defined by claim 25 wherein said system launches a plurality of acoustical waves, via said EMAT Probe, induced magnetically into the tubular wall under inspection, said waves travel in both a counter-clockwise and clock-wise direction simultaneously throughout the circumference of the tubular while traveling longitudinally along the surface of the tubular.

27. The system and apparatus of claim 26 wherein said clockwise and counter-clockwise ultrasonic acoustical wave signals coincide and meet directly below said transmitter and receiver coils.

28. The system of claim 27 wherein said computer processes data received from said probe, comparing said data with preset parameters, thus detecting flaws by denoting shifts in arrival time at a zero crossing of said clock-wise and counter-clockwise ultrasonic wave signals.

29. The system of claim 28 wherein said computer processes data received from said probe, comparing said data with preset parameters, thus detecting flaws by denoting the amplitude of said ultrasonic wave signals.

30. The system of claim 29 wherein said computer processes data received from said probe, comparing said data with preset parameters, thus detecting flaws by denoting echoes reflected back to the receiver.

31. The system of claim 30 wherein said computer processes data received from said EMAT Probe, detecting flaws in longitudinal welds along pipe or tanks by electrically connecting the receiver coil in one EMAT with the transmitter coil in another EMAT bridging said weld.

32. The system of claim 31 wherein said EMATs, arranged on either side of a weld line, detects flaws in the weld and throughout the full circumference of the tubular wall by interpreting signals transmitted and received simultaneously by each EMAT.

33. The system of claim 32 wherein said apparatus utilizes a plurality of wave forms and EMAT types.

34. The system of claim 33 wherein said wave form signals are nonperpendicular to the inspection surface when inspecting fluidized tubulars.

35. A portable, magnetic acoustic transducer probe and system for inspecting operable piping systems for defects comprising:
   a) a movable carriage positionable externally on said pipe;
   b) means for moving said carriage along said pipe;
   c) a transducer means mounted on said carriage;
   d) a permanent magnet mounted on said transducer means so that the north pole of said magnet is held close to the surface of said pipe when said carriage is positioned on said pipe;
   e) interposed transmitter and receiver coils located on said transducer means having precise interfaced loops mounted between said permanent magnet and said pipe surface;
   f) a wear plate covering said coils attached to said transducer means held in springable, sliding, contact with said pipe;
   g) an electronic means located on said carriage for receiving and transmitting signals to and from said transducer coils;
   h) a controller means located remotely and connected electrically by an umbilical cord to said electronic means for controlling signals sent to said carriage;
   i) a data processor means for transmitting signal waves to said transducer coils and processing data received from said coils while scanning longitudinally along said pipe;
   j) a plurality of ultrasonic waves, induced magnetically into the wall of said pipe simultaneously in a clockwise and counter-clockwise direction around the circumference of said pipe; and
   k) a software program loaded into said data processor having predetermined parameters for determining defects throughout said pipe wall by comparing shifts in the arrival times of said waves at a set point of incidence, amplitude of said signal, and comparison of echo signals during the interval between each round trip signal with that of a predetermined echo setting.

36. A portable, magnetic acoustic transducer probe and system for inspecting operable piping systems for defects according to claim wherein said permanent magnet is a plurality of disks arranged in pairs and mounted so as only the north pole of each magnet is exposed to said coils.

37. A portable, magnetic acoustic transducer probe and system for inspecting operable piping systems for defects according to claim wherein said carriage has a plurality of said transducers.

38. A portable magnetic acoustic transducer probe and system for inspecting operable piping systems for defects according to claim 37 wherein said carriage and said transducers are converted for use on large storage tanks.

39. A method for using the apparatus and system as defined or encompassed by claim 37 comprising the steps of:
   a) powering up said data processor and control system;
   b) setting the parameters by establishing the tone burst frequency, amplitude, number of cycles, time duration, and preamp cycle time;
   c) setting signal digitalization frequency and number of wave forms;

d) establishing the display update frequency, time of signal arrival value, display time, size of least squares fit, zero crossing and second window options;

e) fine tuning said settings;

f) choosing type of scan by utilizing one or more transducers;

g) positioning said carriage on said pipe;

h) performing inspection of said pipe while traveling longitudinally along said pipe;

i) controlling the movement of said probe carriage remotely from said controller;

j) visually monitoring each inspection run;

k) recording and storing all inspection data in said data processor;

l) printing each inspection data report; and l) interpreting wave form signal deviations based on preset parameter comparisons.

* * * * *